US006440736B1

(12) United States Patent
Logtenberg et al.

(10) Patent No.: US 6,440,736 B1
(45) Date of Patent: Aug. 27, 2002

(54) ALTERING THE PROPERTIES OF CELLS OR OF PARTICLES WITH MEMBRANES DERIVED FROM CELLS BY MEANS OF LIPID-MODIFIED PROTEINACEOUS MOLECULES

(75) Inventors: Tom Logtenberg, CH Nieuwegein; Cornelis Adriaan De Kruif, VN Utrecht, both of (NL)

(73) Assignee: U-BiSys B.V. (NL)

( * ) Notice: Subject to any disclaimer, the term of this patent is extended or adjusted under 35 U.S.C. 154(b) by 0 days.

(21) Appl. No.: 09/418,563

(22) Filed: Oct. 15, 1999

(30) Foreign Application Priority Data

Oct. 16, 1998 (EP) .............................................. 98203482

(51) Int. Cl.$^7$ ................................................. C12N 5/00
(52) U.S. Cl. ........................................ 435/375; 435/325
(58) Field of Search ............................. 424/93.21, 375, 424/325

(56) References Cited

U.S. PATENT DOCUMENTS 5,374,548 A * 12/1994 Caras .......................... 424/450

OTHER PUBLICATIONS

Abken, H. et al. "Can combined T–cell– and antibody–based immunotherapy outsmart tumor cells?" *Trends [in] Immunology Today* (Jan. 1998) 19(1):2–5.

Abken, H. et al. "Chimeric T–cell receptors: highly specific tools to target cytotoxic T–lymphocytes to tumor cells," *Cancer Treatment Reviews* (1997) 23:97–112.

Bennett, S. R. M et al. "Help for cytotoxic–T–cell responses is mediated by CD40 signalling," *Nature* (Jun. 4, 1998) 393:478–480, Letters to Nature.

Berd, D. et al. "Autologous, Hapten–Modified Vaccine as a Treatment for Human Cancers," *Seminars in Oncology* (Dec. 1998) 25(6):646–653.

Boder, E. T. et al. "Yeast surface display for screening combinatorial polypeptide libraries," *Nature Biotechnology* (Jun. 1997) 15:553557.

Brocker, T. et al. "New simplified molecular design for functional T cell receptor," *Eur J Immunol* (1993) 23:1435–1439.

De Kruif, J. et al. "Biosynthetically lipid–modified human scFv fragments from phage display libraries as targeting molecules for immunoliposomes," *FEBS Letters* (1996) 399:232–236.

De Kruif, J. et al. "Rapid selection of cell subpopulation–specific human monoclonal antibodies from a synthetic phage antibody library," *Proc Natl Acad Sci USA* (Apr. 1995) 92:3938–3942.

De Kruif, J. et al. "Selection and Application of Human Single Chaing Fv Antibody Fragments from a Semi–synthetic Phage Antibody Display Library with Designed CDR3 Regions," *J Mol Biol* (1995) 248:94–105.

Devitt, A. et al. "Human CD14 mediates recognition and phagocytosis of apoptic cells," *Nature* (Apr. 2, 1998) 392:505–509.

Escola, J–M. et al. "Selective Enrichment of Tetraspan Proteins on the Internal Vesicles of Multivesicular Endosomes and on Exosomes Secreted by Human B–lymphocytes," *The Journal of Biological Chemistry* (Aug. 7, 1998) 279(32):20121–21027.

Eshhar, Z. "Tumor–specific T–bodies: towards clinical application," *Cancer Immunol Immunother* (1997) 45:131–136.

Eshhar, Z. et al. "Specific activation and targeting of cytotoxic lymphocytes through chimeric single chains consisting of antibody–binding domains and the γ or ζ subunits of the immunoglobulin and T–cell receptors," *Proc Natl Acad Sci USA* (Jan. 1993) 90:720–724.

Francisco, J. A. et al. "Transport and anchoring of β–lactamase to the external surface of *Escherichia coli*," *Proc Natl Acad Sci USA* (Apr. 1992) 89:2713–2717.

Freeman, S. M. et al. "Immune system in suicide–gene therapy," *The Lancet* (Jan. 4, 1997) 349:2–3.

Gage, F. H. "Cell Therapy," *Nature* (Apr. 30, 1998) 392 Supp.:18–24.

Ghrayeb, J. et al. "Nine Amino Acid Residues at the NH$_2$–terminal of Lipoprotein Are Sufficient for Its Modification, Processing, and Localization in the Outer Membrane of *Escherichia coli*," *The Journal of Biological Chemistry* (Jan. 10, 1984) 259(1):463–487.

Gong, J. et al. "Induction of antitumor activity by immunization with fusions of dendritic and carcinoma cells," *Nature Medicine* (May 1997) 3(5):558–561.

Gosselin, E. J. et al. "Enhanced Antigen Presentation Using Human Fcγ Receptor (Monocyte/Macrophage)–Specific Immunogens," *The Journal of Immunology* (Dec. 1, 1992) 149(14):3477–3481.

Graziano, R. F. et al. "Construction and Characterization of a Humanized Anti–γ–Ig Receptor Type I (FcγRI) Monoclonal Antibody," *The Journal of Immunology* (1995) 155:4996–5002.

(List continued on next page.)

*Primary Examiner*—Robert A. Schwartzman
(74) *Attorney, Agent, or Firm*—Morrison & Foerster LLP

(57) ABSTRACT

A processs for altering the properties of a cell or cell membrane involves the contacting of the cell or cellular membrane with a lipid-modified protein under conditions wherein the lipid portions anchor themselves to the cellar membrane and position the protein portion of the molecule so that it imparts to the cell or cell membrane one or more new characteristics resulting from the introduction of the protein. Recombinant and cell-free methods for synthesis of the lipid-modified protein are taught as are kits for altering the properties of cell and/or cell membranes.

21 Claims, 12 Drawing Sheets

OTHER PUBLICATIONS

Figures 2A, 2B:
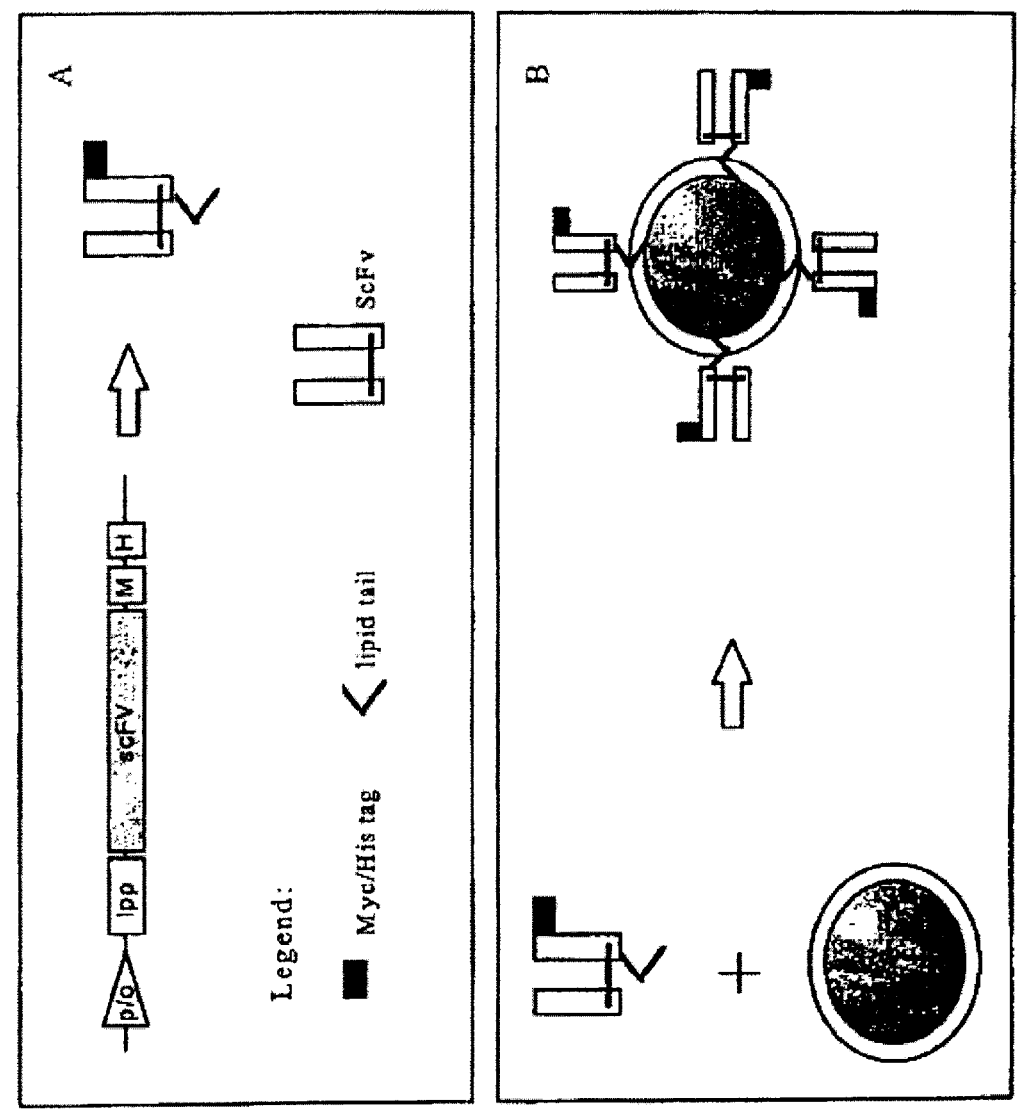

Grouard, G. et al. "Human Follicular Dendtritic Cells Enhance cytokine–Dependent Growth and Differentiation of CD40–Activated B Cells," *The Journal of Immunology* (1995) 155:3345–3352.

Grouard, G. et al. "Human Follicular Dendritic Cells Enhance Cytokine–Dependent Growth and Differentiation of CD40–Activated B Cells," *the Journal of Immunology* (1995) 155:3345–3352.

Haas, C. et al. "An effective strategy of human tumor vaccine modification by coupling bispecific costimulatory molecules," *Cancer Gene Therapy* (1999) 6(3):254–262.

Houghton, A. N. "Cancer Antigens: Immune Recognition of Self and Altered Self," *J Exp Med* (Jul. 1994) 180:1–4, Commentary.

Hwu, P. et al. "In Vivo Antitumor Activity of T Cells Redirected with Chimeric Antibody/T–Cell Receptor Genes," *Cancer Research* (Aug. 1, 1995) 55:3369–3373.

Jin, L. et al. "Targeted expansion of genetically modified bone marrow cells," *Proc Natl Acad Sci USA* (Jul. 1998) 95:8093–8097.

Kafri, T. et al. "Sustained expression of genes delivered directly into liver and muscle by lentiviral vectors," *Nature Genetics* (Nov. 1997) 17:314–317, Letter.

Keene, J–A. et al. "Helper Activity is Required for the In Vivo Generation of Cytotoxic T Lymphocytes," *J Exp Med* (Mar. 1982) 155:768–782.

Kwiatkowska, K. et al. "Signaling pathways in phagocytosis," *BioEssays* (1999) 21:422–431.

Laukkanen, M–L., et al. "Functional Immunoliposomes Harboring a Biosynthetically Lipid–Tagged Single–Chain Antibody," *Biochemistry* (1994) 33:11664–11670.

Laukkanen, M–L., et al. "Lipid–tagged antibodies: bacterial expression and characterization of a lipoprotein–single–chain antibody fusion protein," *Protein Engineering* (1993) 6(4):449–454.

Liu, C. et al. "FcγRI–Targeted Fusion Proteins Results in Efficient Presentation by Human Monocytes of Antigenic and Antagonist T Cell Epitopes," *J Clin Invest* (Nov. 1996) 98(9):2001–2007.

Melcher, A. et al. "Tumor immunogenicity is determined by the mechanism of cell death via induction of heat shock protein expression," *Nature Medicine* (May 1998) 4(5):581–587.

Nawrocki, S. et al. "Genetically modified tumour vaccines—where we are today," *Cancer Treatment Reviews* (1999) 25:29–46.

Pack, P. et al. "Improved Bivalent Miniantibodies, with Identical Avidity as Whole Antibodies, Produced by High Cell Density Fermentation of *E. coli*," *Bio/Technology* (Nov. 1993) 11:1271–1277.

Ridge, J. P. et al. "A conditioned dendritic cell can be a temporal bridge between a $CD4^+$ T–helper and a T–killer cell," *Nature* (Jan. 4, 1998) 393:474–477.

Rosenberg, S. A. "The Immunotherapy and Gene Therapy of Cancer," *Journal of Clinical Oncology* (Feb. 1992) 10(2):180–199, Karnofsky Memorial Lecture.

Rosenberg, S. A. et al. "Use of tumor–Infiltrating Lymphocytes and Interleukin–2 in the Immunotherapy of Patients with Metastatic Melanoma, A Preliminary Report," *The New England Journal of Medicine* (Dec. 22, 1988) 319(25):1676–1680, Special Report.

Rusiñol, A. E. et al. "In Vitro Reconstitution of Assembly of Apolipoprotein B48–containing Lipoproteins," *The Journal of Biological Chemistry* (Mar. 21, 1997) 272(12):8019–8025.

Sallusto, F. et al. "Efficient Presentation of Soluble Antigen by Cultured Human Dendritic Cell Is Maintained by Granulocyte/Macrophage Colony–stimulating Factor Plus Interleukin 4 and Downregulated by Tumor Necrosis Factor α," *J Exp Med* (Apr. 1994) 179:1109–1118.

Schirrmacher, V. et al. "Human tumor cell modification by virus infection: an efficient and safe way to produce cancer vaccine with pleiotropic immune stimulatory properties when using Newcastle disease virus," *Gene Therapy* (1999) 6:63–73.

Schoenberger, S. P. et al. "T–cell help for cytotoxic T lymphocytes is mediated by CD40–CD40L interactions," *Nature* (Jun. 4, 1998) 393:480–483, Letters to Nature.

Simons, K. et al. "Functional rafts in cell membranes," *Nature* (Jun. 5, 1997) 387:569–572.

Smith, G. P. "Filamentous fusion Phage: Novel Expression Vectors That Display Cloned Antigens on the Virion Surface," *Science* (Jun. 14, 1985) 228:1315–1317.

Undenfriend, S. et al. "How Glycosyl–Phosphatidylinositol–Anchored Membrane Proteins are Made," *Annu Rev Biochem* (1995) 64:563–591.

Vermorken, J. B. et al. "Active specific immunotherapy for stage II and stage III human colon cancer: a randomised trial," *The Lancet* (1999) 353:345–50.

Yee, C. et al. "Prospects for adoptive T cell therapy," *Current Opinion in Immunology* (1997) 9:702–708.

Zitvogel, L. et al. "Eradication of established murine tumors using a novel cell–free vaccine: dendritic cell–derived exosomes," *Nature Medicine* (May 1998) 4(5):594–600.

* cited by examiner

Figure 1A
Figure 1B
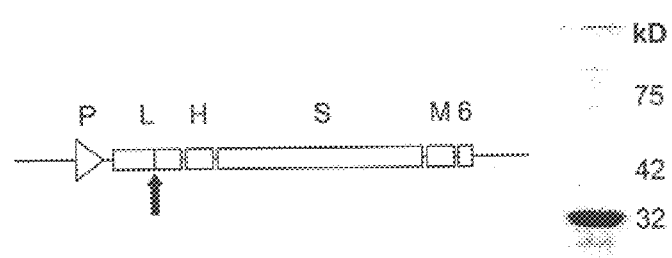
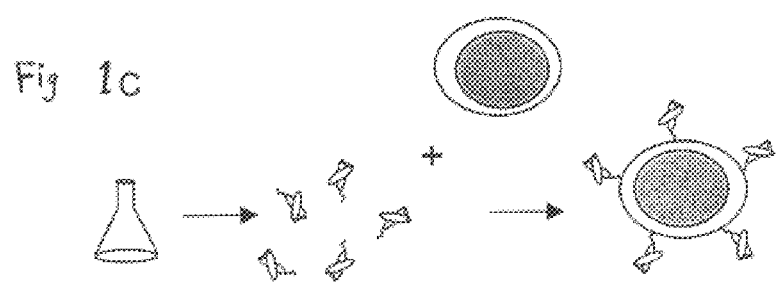
Fig 1c

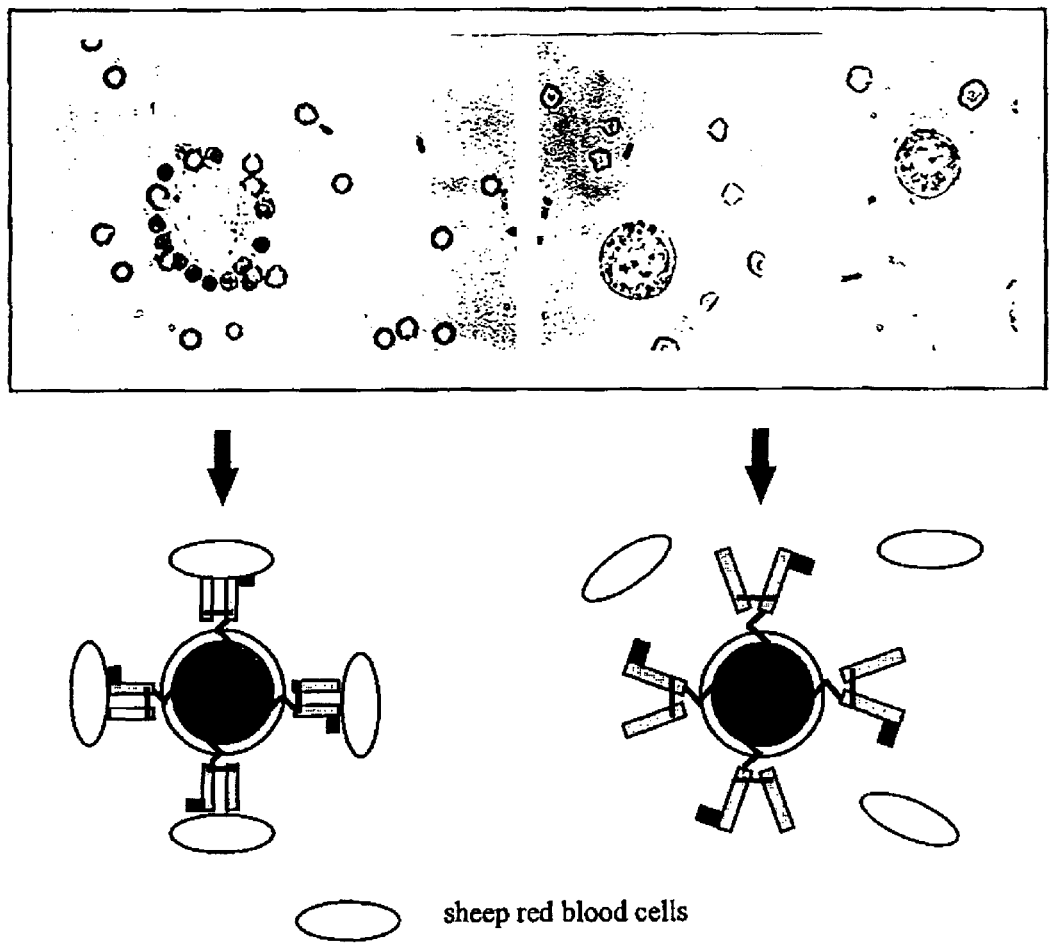

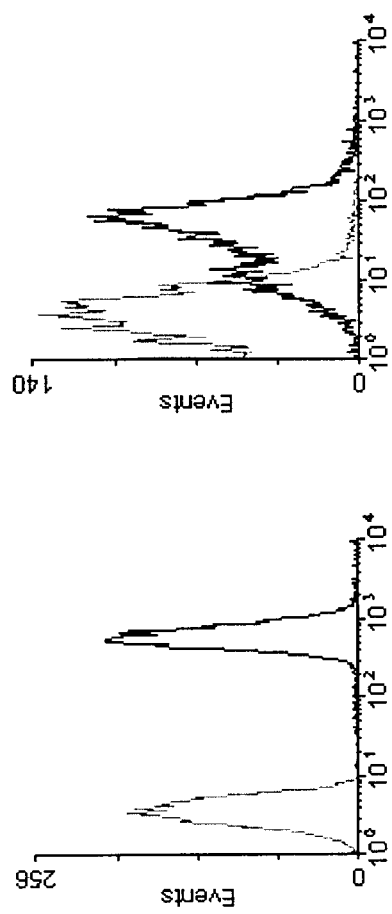
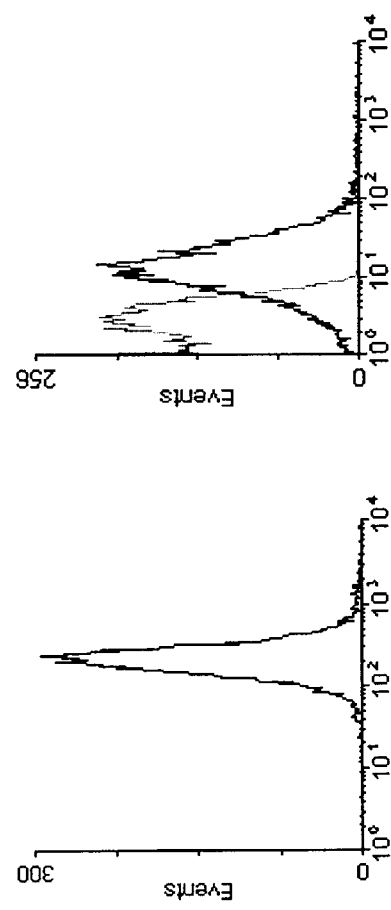
Figure 6A
Figure 6B
Figure 6C
Figure 6D

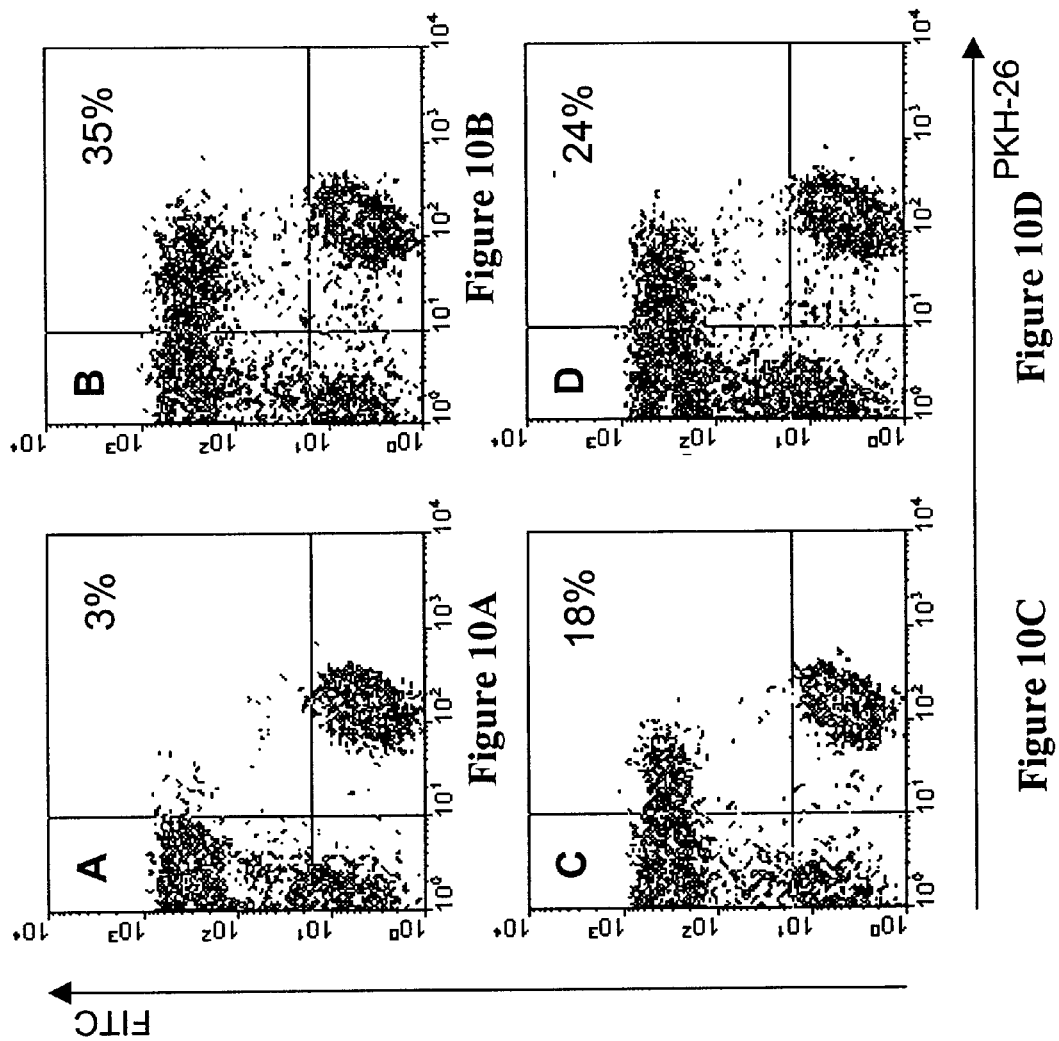

ALTERING THE PROPERTIES OF CELLS OR OF PARTICLES WITH MEMBRANES DERIVED FROM CELLS BY MEANS OF LIPID-MODIFIED PROTEINACEOUS MOLECULES

The present invention relates to pharmaceutical compositions, methods, kits, cells and particles containing membranes derived from cells. More specifically, the invention relates to a novel method of altering the properties of cells and of particles with membranes derived from cells.

In 1993 Laukanen et al. have described a method that facilitates the addition of a hydrophobic membrane anchor to single chain variable fragment (scFv) antibody fragments expressed in E. coli (Laukanen et al., Protein Engineering 6:449–454,1993). This method relies on the fusion of the signal peptide and 9 N-terminal residues of the bacterial lipoprotein (lpp) to a scFv antibody fragment. It was previously shown by Ghrayeb et al (1984) that only the signal peptide and nine amino acids of the mature lpp are required for the correct processing and transport of an lpp fusion protein to the outer membrane of E. coli. Laukanen (Laukanen et al., Biochemistry 33: 11G64–11670,1994) and de Kruif (de Kruif et al., FEBS letters 399:232–236, 1996) demonstrated that the lipid-modified antibody fragment can be expressed in E. coli and that the lipid-modified scFv is inserted into he periplasmic leaflet of the outer membrane and not on the outside of tee bacterium. After preparation of membrane extracts from the E. coli cells and purification of the lipid-modified scFv, it was shown that these molecules retain their binding specificity and can be functionally reconstituted into artificial vesicles composed of a lipid bilayer.

Although possible, the loading of artificial vesicles requires a lengthy biochemical procedure which is not very efficient and requires large amounts of lipid-modified proteinaceous molecules for effective incorporation of said molecules into the artificial lipid bilayer. Moreover, the process is not very controllable as to the orientation of said molecules in the lipid bilayer. In addition, it was found that the resulting vesicles shed the lipid-modified proteinaceous molecules quite rapidly in vivo. These disadvantages are not easily bypassed by optimising the procedure since the underlying reasons for these phenomena are unknown. The limitations of the procedure severely inhibit the practical applications for artificial lipid bilayers loaded with lipid-modified proteinaceous molecules.

The most common approach to change the properties of cells is the introduction of DNA or RNA into the cells. Subsequent expression of the introduced nucleic acid leads to the presence of novel proteins in intracellular compartments or on the plasma membrane of the cells. DNA is introduced into cells by one of a variety of methods, where upon it is stably integrated in the genomic DNA or remains in the cells as an extra-chromosomal fragment. This strategy is widely used to study the function of the molecule encoded by the introduced DNA or to endow the recipient cell with properties encoded by the introduced DNA.

Cell therapy is a strategy for the treatment of many diseases. The aim of cell therapy is to replace or repair damaged tissue or organs or to enhance the biological function of cells. ?or cell therapy, cells are isolated from a tissue or organ and manipulated ex vivo, for example by adding growth factors to cells in tissue culture with the aim to increase their number (Gage et al, Nature 392 (supplement):18–24, 1998). It is also common practise in cell therapy to introduce DNA into cells and, by using selectable markers such as antibiotic resistance, select cells that stably or transiently express the introduced DNA. The aim of this approach is to endow the recipient cell with novel properties. For example, DNA encoding a growth factor receptor may be introduced ex vivo into bone marrow cells and cells that express the growth factor receptor may be re-infused into a recipient organism. Treatment of the organism with the growth factor then results in the in vivo expansion of manipulated bone marrow cells expressing the growth factor receptor (Jin et al, Proc. Natl. Acad. Sci. USA 95:8092–8097,1998). In another application, T lymphocytes may be retrovirally transduced with DNA encoding a fusion protein consisting of a scFv antibody specific for folate-binding protein joined to the Fc-receptor gamma chain. After selection and expansion of T cells expressing the fusion protein and re-infusion, it was shown in an animal model that the T lymphocytes reacted against tumour cells (Hwu et al., Cancer Res. 55:3369–3373, 1995). The method of introducing DNA into cells with the aim to alter their properties is time-consuming, requires the introduction of foreign genetic material into human cells and is constrained by the inefficiency of DNA transfer into some cell types, especially freshly-isolated cells.

The present invention discloses a novel use of lipid-modified proteinaceous molecules. In the present invention lipid-modified proteinaceous molecules are contacted with cells and/or with particles containing membranes derived from cells. Upon contact the lipid-modified proteinaceous molecules are inserted into the membrane of a cell and/or of a particle with a membrane derived from a cell. This novel use not only enables a completely novel approach to manipulate cells and/or particles containing membranes derived from cells. But in addition, this process is very efficient, requiring relatively low amounts of lipid-modified proteinaceous molecules for effective incorporation by a cell and or a particle derived from a cell. Moreover, the lipid-modified proteinaceous molecules added to said cell and/or said particle are surprisingly stable in vivo. The proteinaceous molecules to be taken up by said cells and/or said particles are produced as lipid-modified molecules that spontaneously attach to membranes without using biochemical coupling procedures. This procedure can be used to endow the recipient cells with molecules that act as signaling molecules or otherwise affect the properties of the cells, for example in their capacity to recognise a target or to home to a particular tissue or organ. The present invention provides a rapid and effective alternative for methods that rely on introduction and expression of nucleic acids into cells, resulting in the expression of plasma membrane-associated proteinaceous molecules. Since the present invention is independent of gene transfer and rapid the invention possesses discrete advantages over the conventional methods based on gene transfer. Although many gene transfer methods have been devised some cell types have remained refractory to efficient gene transfer. The present invention is independent of gene transfer efficiency and thus provides a completely different and versatile method for the insertion of proteinaceous molecules in the membranes of cells and/or of particles with membranes derived from cells. Moreover, the process of adding the proteinaceous molecules is fast, thus obviating the obligatory incubation period for obtaining maximal protein expression following gene transfer.

One of the most prominent applications of the present invention lies in the field of cell therapy as a strategy for the treatment of human diseases.

The present invention provides a novel method to alter the properties of cells and/or of particles containing membranes derived from cells. The present invention does not rely on the transfer of a nucleic acid but instead directly supplies the desired protein to the membrane enabling a rapid alteration of the properties of the cell and/or the particle with a membrane derived from a cell. The present invention offers advantages over conventional nucleic acid transfer in that it is fast and suitable for a wide variety of cell types including but not limited to primary cells isolated from a human.

SUMMARY OF THE INVENTION

One aspect of the invention is to provide a method for efficiently attaching proteinaceous molecules to the membranes of cells and or of particles containing membranes derived from cells. The method is rapid, leads to the incorporation of high numbers of molecules in the outer membrane, requires minimal handling of said cells and/or said particles, does not require introduction of genetic material into cells and appears to be generally applicable to all cell types and all particles containing membranes derived from cells. A major advantage for therapeutical application is that the method can be used to efficiently incorporate proteinaceous molecules in the plasma membrane of cells that are freshly-isolated from a tissue or organ, which difficult to achieve with other methods. In addition, the method offers the advantage that attachment of molecules to the plasma membrane of cells can be accomplished in a very short period of time.

In one embodiment of the invention a process is provided for providing a cell and/or a particle with a membrane derived from said cell with an additional proteinaceous molecule wherein said process comprises contacting said cell or said particle with a proteinaceous molecule, said molecule comprising at least one hydrophobic moiety. The method of contacting may be any method wherein the lipid-modified proteinaceous molecule is presented from the outside to said cell and/or said particle. In one embodiment of the invention said hydrophobic moiety comprises a stretch of hydrophobic amino acids capable of inserting itself in said membranes. In another embodiment of the invention said hydrophobic part comprises one or more fatty acid chains. In a preferred embodiment, the invention provides a process for providing a cell and/or a particle with a membrane derived from a cell with an additional proteinaceous molecule said process comprising contacting said cell and/or said particle with a lipid-modified proteinaceous molecule. In this preferred embodiment the proteinaceous molecule is linked to one or more lipids, a process termed lipidation, as a result of one or more lipidation signals. One lipidation signal resulting in one lipid tail is sufficient for a rapid transfer and anchorage of the lipid-modified proteinaceous molecule to the outer membrane of a cell and/or of a particle with a membrane derived from a cell. However, a second or even more lipidation signals, thus resulting in a lipid-modified proteinaceous molecule with two or more lipid tails, may be added for increased stability of the molecule in the membrane or to increase the stability of a specifically desired three dimensional configuration of said molecule. For example, the construct depicted in FIG. 1 may be modified to contain a second lipidation signal at the 3 prime end of the scFv gene, resulting in a lipid-modified scFv with a lipid tail at both the amino and the carboxyl terminus of the protein.

In one embodiment of the invention the lipidation of the proteinaceous molecule may occur in a cell free system where the lipidation as a result of the lipidation signal is achieved by components added to the cell free system (see for instance Rusinol, A. E. J et al. Biol. Chem. 272, 8019–8025, 1997). In a preferred embodiment of the invention, the lipidation of the proteinaceous molecule is accomplished in a cell. In this preferred embodiment of the invention cellular enzymes are recruited to catalyse the lipidation of the proteinaceous molecules following a signal that is recognised by the lipidation machinery of the cell. In a particularly preferred embodiment of the invention the lipidation of the proteinaceous molecules is performed in bacteria in response to a lipidation signal recognised by the bacterial lipidation machinery. Production of a lipid-modified proteinaceous molecule in bacteria compared to eukaryotic cells generally results in higher yields. Production in bacteria is more cost effective than production in eukaryotic cells. Production of lipid-modified proteinaceous molecules in bacteria, as opposed to eukaryotic cells, for a pharmaceutical application in human and/or animal has furthermore the advantage that bacterial produced pharmaca have a significantly lower propensity for the presence of viruses and/or prions that may be harmful for a human and/or an animal. In one aspect of this particularly preferred embodiment the limidation of the proteinaceous molecules occurs in $E.\ coli$ and the lipidation signal is derived from bacterial lipoprotein. In this particularly preferred embodiment the synthesis and the lipidation of said proteinaceous molecule is accomplished by introducing a recombinant DNA expression plasmid or vector into $E.\ coli$. Glycosylphosphatidylinositol (GPI)-linked proteins form another non-limiting example of a group of proteins from of which the lipidation signal may be incorporated into a proteinaceous moiety to produce the lipid-modified proteinacecus molecules of the invention. GPI-linked proteins are plasma membrane molecules that lack a cytoplasmic tail and are attached to the plasma membrane of cells by a lipid anchor. Despite the lack of a cytoplasmic tail, GPI-linked proteins may operate as signaling molecules, conveying signals to the cell after binding of ligands or antibodies. Cell signaling via GPI-linked proteins may induce a broad variety of cellular responses, including cell activation and differentiation, apoltosis, and secretion of cytokines. Available evidence suggests that signaling via GPI-linked proteins may occur through the physical interaction of the GPI-linked protein with other membrane molecules (Simons et al., Nature 387;569–572, 1997).

In a preferred embodiment of the invention proteinaceous molecules are lipidated as a result of a lipidation signal derived from glycosylphosphatidylinositol (GPI)-linked proteins. In this preferred embodiment the lipidation of the proteinaceous molecules is achieved in eukaryotic cells, preferably yeast cells. Sequences containing the signal leading to the attachment of glycosylphosphatidylinositols moieties to proteins may be found in Udenfriend et al, Annu. Rev. Biochem. 64, 563–591 1995.

Many different paoteinaceous molecules may be used in the present invention. Proteinaceous molecules may be derived from proteins present in nature but may also be generated completely artificially as long as they contain or have added to them a lipidation signal. In a preferred embodiment of the invention the proteinaceous moiety of the lipid-modified proteinaceous molecules is derived from natural proteinaceous molecules with actions near or in membranes. Non-limiting examples of such molecules are receptors, co-receptors, (membrane-bound) ligands, signaling molecules, homing molecules or molecular pumps. on the other hand however, also molecules may be used with no known action in membranes or with actions that normally do not depend on the presence of a membrane.

Artificial proteinaceous molecules, e.g. not present in nature, can upon lipidation also be used for the present invention. Non-limiting examples of this are lipid-modified single chain variable fragments (scFv). Applications of such lipid-modified scFv are manifold, for instance but not limited to application of lipid-modifed scFv specific for a certain type of cell. Such molecules are useful to target cells of the immune system to specific cells in the body thus interfering either positively or negatively with the immune system. One application is to enable a more effective immune response against undesired cells such as malignant cells or virus infected cells. Another application is to interfere with the immune system in a negative way to suppress an undesired immune response and induce a specific tolerance such as is desired in the most common forms of arthritis, insulin-related diabetes or allergies. In these diseases part of the immune system is inadvertently directed to self-antigens or over sensitive to foreign antigens.

In another aspect of the invention the proteinaceous molecule is derived from a proteinaceous molecule active in the immune system so a human or animal. Non-limiting examples are antibodies, fragments derived from antibodies such as fragment antigen binding (FAB) fragments, proteins resembling fragments derived from antibodies such as artificially produced FAB-fragments and T-cell receptors.

In addition, the proteinaceous molecule may be a derivative from other classes of proteins derived from cells of the immune system such as co-stimulatory molecules, heat shock proteins, major histo-compatibility complex (MHC) proteins or antigenic peptides. FAB-fragments generated by cleavage from antibodies or FAB-fragment-like proteins generated artificially will further collectively be referred to as FAB-fragments, In another aspect of the invention a lipid-modified proteinaceous molecule comprises a stretch of amino acids conferring to the proteinaceous molecule the property to interact with a signal-transducing molecule present on the plasma membrane of a cell.

In one aspect of the invention a cell, or a particle with a membrane derived from a cell, is contacted with two or more different types of lipid-modified proteinaceous molecules. The crucial difference being the capability of the lipid-modified proteinaceous molecules to change the property of said cell or said particle in a different way. In this aspect of the invention two or more different types of lipid-modified proteinaceous molecules are used to combine the effect of each type of lipid-modified proteinaceous molecule.

In yet another aspect of the invention the lipid-modified proteinaceous molecules contain an additional signal, designated "purification" tag enabling the easy purification of the lipid-modified proteinaceous molecules during the production process. A non-limiting example of such a purification tag is a polyhistidine sequence or polyhistidine tag. In another embodiment of the invention the lipid-modified proteinaceous molecules contain an additional signal, designated "detection" tag for the detection of the lipid-modified proteinaceous molecules. A non-limiting example of such a detection tag is a short stretch of amino acids derived from the myc-gene product, a so-called myc tag.

In another aspect of the invention is provided a kit with which the invention can be practised to obtain a cell or a particle with a membrane derived from said cell, comprising an additional lipid-modified proteinaceous molecule. This kit minimally contains a lipid-modified proteinaceous molecule but may further contain matters and substances useful to operate the invention such as sterile bags, culture materials, buffers and quality assurance materials such as materials in the form of scFv to assay the amount of lipid-modified proteinaceous molecule loaded onto a cell or a particle containing a membrane derived from a cell.

In one embodiment of the invention is provided a vector for the production of lipid-modified proteinaceous molecules in cell, preferably bacterial or yeast cells. Said vector comprises at least one open reading frame which minimally encodes for at least one protein of interest and at least one lipidation signal. Said open reading frame may further comprise additional elements coding for a detection tag and/or a purification tag.

It is clear to a person skilled in the art that only the essential part or parts of a protein are required in the lipid-modified proteinaceous molecules of the invention. Thus deletions/insertions or mutations in non-relevant parts of the protein molecule of which the proteinaceous moiety in the lipid-modified proteinaceous molecule is derived are anticipated to be equally effective as the entire protein molecule.

It is also clear to a person skilled in the art that the protein moiety of the lipid-modified proteinaceous molecule may contain further functional units derived from, different proteins existing in nature or artificial to broaden the functionality of said lipid-modified proteinaceous molecule.

It is clear that the lipid-modified proteinaceous molecules of the invention, when contacted with a cell or a particle with a membrane derived from a cell, will preferentially attach to first membrane encountered and orient themselves such that the proteinaceous moiety is directed outward. However, active processes, such as endocytosis, lead to entry of the lipid-modified proteinaceous molecules or derivatives thereof into the interior of the cell or the particle with a membrane derived from a cell.

An important aspect of the invention is the alteration of the properties of a cell or a particle containing a membrane derived from a cell by providing said cell or said particle with additional lipid-modified proteinaceous molecules. Said cell may be any type of prokaryotic or eukaryotic cell. In a preferred embodiment of the invention said cell is a human cell. In a preferred embodiment of the invention the properties of tumour infiltrating lymphocytes (TILs) or lymphocyte activated killer cells (LAKs) are altered by providing the cells with additional lipid-modified proteinaceous molecules. TILs and LAKs are cells of the immune system that have been expanded in vitro with interleukin-2 (IL-2) to obtain large numbers of cells that have anti-tumour effect. After in vitro expansion, these cells are re-infused into patients with cancer where they can exert their anti-tumour effect (Rosenberg et al, N. Eng. 4. Med. 319, 1676–1680, 1988; Rosenberg et al, Clin. Oncol. 10, 180–199, 1992). Infusion of polyclonal populations of TILs has yielded low response rates, short response duration's, poor localisation of the T-cells to tumour sites and severe toxicity's associated with concurrent administration of high doses of IL-2 (Yee et al, Current Opin. Immunol. 9, 702–708, 1997). To overcome some of these problems, in vivo expanded T-cells have been transfected with DNA encoding receptors for recognition of tumour cells. In some applications, DNA encoding a scFv has beer. introduced in in vitro expanded T-cells (Eshar et al, Proc. Natl. Acad. Sci. USA 90, 720–724,1993; Brocker et al, Eur. J. Immunol. 23, 1435, 1993). In vivo studies with such gene-modified T-cells, endowed with a scFv specific for tumour cells have shown promising results (Abken et al, Immunol. Today, 19, 2–5, 1998). A drawback of such approaches is the use of gene-modified cells for therapy and the efficiency of producing sufficient numbers of gene-modified cells (Abken et al, Cancer Treat. Rev. 23 (2), 97–112, 1997; Abken et al, Immunol. Today, 19, 2–5, 1990). By using lipid-modified scFv, these limitations can be overcome. This approach does not involve introduction of genes into cells to be re-infused in patient and is the addition of the desired scFv to the cells is very efficient.

Thus in a preferred embodiment of the invention TILs or LAKs are supplied with additional lipid-modified proteinaceous molecules, preferably lipid-modified scFv, to alter the properties of these cells, preferably a property enabling or improving the homing of said TILs or LAKs to tumour sites. In a preferred embodiment of this invention said lipid-modified scFv are directed to endothelial cells of growing blood vessels, preferably directed to blood vessels in tumours.

In a preferred embodiment of the invention particles with membranes derived from cells are contacted with lipid-modified proteinaceous molecules. Particles containing membranes derived from cells are particles that are for example formed after mechanical disruption of cells or solubilisation of cells in detergents. Particles containing membranes derived from cells are also produced by living cells such as for example exosomes (Escola et al., J. Biol. Chem. 273, 20121–20127,1998 and Zitvogel et al., Nat. Med. 4, 594–600, 1998) or such as enveloped viruses, very low density lipoprotein (VLDL), low density lipoprotein (LDL) and chilomicron particles. Particles with membranes derived from cells may be provided with additional lipid-modified proteinaceous molecules to alter the properties of said particles. Lipid-modified proteinaceous molecules may be contacted with said particles directly or alternatively, lipid-modified proteinaceous molecules may be contacted with cells producing said particles. In the latter case said lipid-modified proteinaceous molecules are incorporated into said particles during their production. In a preferred embodiment of the invention said lipid-modified proteinaceous molecules provide the particles with membranes derived from cells with a new target cell specificity. Such specificity may be added through, for example, a scFv molecule with a specificity for an antigen on the surface of a cell type previously not belonging to the target cell pool of said particle.

The present invention provides methods for the addition of lipid-modified proteinaceous molecules to the membranes of cells and/or of particles with membranes derived from cells.

The present invention is useful to solve one of the problems associated with viral vectors used in the transfer of foreign genetic to target cells. In therapeutic applications of viral vectors in the field of gene therapy, target cells consists of cells from an entire organ such as the liver or an entire group of cells dispersed in the body such as the hematopoietic stem cells, metastasised tumour cells or virus infected cells. Is it for delivery of foreign genetic material to organs sometimes possible to deliver the viral vector only to the cells of that organ (for instance through physical means or surgery). For dispersed target cells, delivery of the viral vector to the target cells can only be accomplished through the bloodstream. To avoid uptake of the viral vector by other cells, some kind of specificity for the target cell must be introduced into the viral vector. This so-called targeting of viral vectors is a very active field of research. For enveloped viruses, i.e. surrounded by a membrane, most approaches to targeting of viral vectors depend on modification of the viral envelop protein. Said viral envelop protein is present on the outside of the viral membrane and is responsible for target cell recognition and, in most cases, for fusion of the viral membrane with a cellular membrane. Approaches to modify the viral envelop protein and other targeting approaches such as those that rely on the incorporation of specific viral (co)-receptors in the membrane of the virus particle have the serious disadvantage that changing the targeting specificity is a lengthy and rather unpredictable process. In addition, more often than not the viral vector provided with the new target cell specificity is much less efficiently produced, or much less infective when compared to the unmodified virus. With the methods of the invention, enveloped viral vectors may be provided with novel target cell specificities in a rapid, reproducible way.

In a preferred embodiment of the invention a cell is genetically modified before or after being contacted with lipid-modified proteinaceous molecules. For example, it is advantageous to introduce a gene encoding the Herpes Simplex Virus (HSC) thymidine kinase (tk) into the cell as a build in safeguard against undesired effects of said cells once inside the body. The cells expressing the HSV-tk are sensitive to killing by the drug gangcyclovir (Freeman et al, SM Lancet 349, 2–3, 1997). Another example is the introduction of a cytokine gene such as IL-2 into a tumour cell treated with lipid-modified proteinaceous molecules, wherein expression of IL-2 enhances the immune response against the tumour cells. We have developed a procedure that allows the rapid and efficient insertion of lipid-tagged (LT) proteins into the membrane of prokaryotic and eukaryotic cells. The procedure appears to be applicable to most eukaryotic cell types including freshly isolated cell populations. LT-scFv antibody fragments inserted into cell membranes were shown to remain fully functional, capable of binding soluble and membrane-bound molecules expressed by other cells. LT-scFv specific for molecules expressed by antigen presenting cells and attached to the membrane of tumor cells mediated efficient phagocytosis of the tumor cells. Because of the ease and efficiency of production and purification of LT-proteins and the method of attaching them to freshly isolated tumor cells, this approach may be used in cellular vaccination strategies with modified autologous tumor cells capable of eliciting a vigorous anti-tumor response.

His-tagged LT-scFv's were expressed in *E. coli* and purified using metal affinity chromatography. To achieve even higher purity, additional affinity chromatography employing the myc tag fused to the LT-scFv fragment and an anti-myc monoclonal antibody may be used (Laukkanen el al. 1994, Biochemistry. 33:11664–11670). The N-terminal portion of the recombinant lipoprotein consists of a glyceryl cysteine to which three fatty acids are attached. This lipid group is highly hydrophobic and its natural function is to anchor bacterial LPP within the outer membrane of *E. coli* (Grayeb et al. 1984, J. Biol. Chem. 259:463–467). We presume that the lipid-modified proteins localize in the cell membranes in a similar fashion.

Peptides and proteins, including scFv antibody fragments, have been displayed on the surface of a variety of cell types including filamentous phage particles (Smiths, G. P. 1985, Science. 228:1315–1317), bacteria (Francisco, J. A. et al., 1992, Proc. Natl. Acad. Sci. USA, 89:2713–2717), yeast Boder E. T. et al. 1997, Nat. Biotechnol. 15:553–557) and mammalian cells (Eshhar, Z. 1997, Cancer Immunol. Immunother. 45:131–136). In these systems, surface display is achieved by genetic fusion of the DNA encoding the protein of interest to DNA encoding a host cell surface or coat protein, followed by introduction of the fusion construct into the host cell and selection of transfected cells. The method described here differs from these approaches in that display of lipid-modified proteins by membrane insertion does not require introduction of DNA into the cell nor does it require culture and selection of cells. Membrane-insertion of lipid-modified proteins is completed within 30 minutes, requires a simple incubation and washing step and is nearly 100% efficient. CD14 and the Fcγ receptors CD32 and CD64 belong to a group of cell surface receptors engaged in phagocytosis by various types of phagocytes including macrophages, dendritic cells, and monocytes (Kwiatkowska, K. et al. 1999, BioEssays. 21:422–431). CD14 mediates the recognition and phagocytosis of apoptotic cells via an as yet unidentified ligand expressed by apoptotic but not by viable cells (Devitt, A. et al. 1998, Nature 392:505–509), whereas CD32 and CD64 mediate phagocytosis of IgG-opsonized particles such as microorganisms. We reasoned that an anti-CD14 LT-scFv fragment anchored to the cell membrane of a viable cell could be used to mimic the putative CD14 ligand on apoptotic cells.

Similarly, we anticipated that LT-scFv's specific for CD32 and CD64 would render the recipient cell susceptible to phagocytosis mediated via Fcγ receptors. Indeed, cells modified with LT-scFv specific for CD14, CD32 and CD64 were efficiently phagocytosed by monocytes and macrophages. We conclude that LT-scFv anchored to cell membranes act as surrogate receptors that are capable of altering the properties of the recipient cell.

Monocytes, macrophages and dendritic cells also function as antigen presenting cells. Uptake of antigen-antibody complexes via Fcγ receptors such as CD32 and CD64 results in the capture and internalization of low concentrations of antigens, followed by processing and presentation to T lymphocytes For example, when antigens are internalized as immune complexes through CD32 by dendritic cells there is a marked increase in the efficiency of T cell activation in response to low concentrations of antigen (Sallusto, F et al. 1994, J. Exp. Med. 179: 1109–1114). Targeting antigen to either CD32 or CD64 on monocytes reduces the concentration of antigen required for T cell activation approximately 1000-fold (Gosselin, E. J. et al. 1932, J. Immunol. 149:3477–3481). Peptides fused to anti-CD64 mAb 22, used as an LT-scFv fragment in this study, were recently shown to be up to 1000-fold more efficient than the non-fused peptides for T cell stimulation when targeted to monocytes (Liu, C. et al. 1999, J. Clin. Invest. 98:2001–2007). Extrapolating from these data, we predict that targeting irradiated tumor cells to antigen-presenting cells via membrane bound LT-scFv's will be an attractive method for activation of anti-tumor T cell responses. Notably, the method does not require identification and cloning of tumor antigens but instead uses the whole tumor cell as a source of tumor antigens.

Furthermore, more than one specificity of scFv may be displayed on a single tumor cell. Thus, incorporation of an anti-CD40 LT-scFv, in addition to a targeting antibody for antigen presenting cells, may replace the requirement for $T_H$ cells in the activation of antigen presenting cells by mimicking the CD40 ligand (Ridge, J. P. et al. 1998, Nature. 393:474–478) Ex vivo alteration of the properties of autologous tumor cells and re-infusion of the modified cells in cancer patients, or animal models of cancer, has been actively explored as a vaccination strategy for the treatment of cancer. Collectively, these approaches aim at increasing the immunogenicity of the tumor cells resulting in the induction of anti-tumor responses. Tumor cells have been genetically modified to secrete cytokines or express co-stimulatory molecules that stimulate cells of the immune system (Nawrocki, S. et al. 1999, Cancer Treat. Rev. 25:29–46). Alternatively, tumor cells have been modified by viral infection (Schirrmacher, V., et al. 1999, Gene Ther. 6:63–73), bispecific molecules (Haas, C. et al. 1999, Cancer Gene Ther. 6:254–262), haptenization of membrane molecules (Berd, D. et al. 1998, Semin. Oncol. 25: 646–653)or by fusion of tumor cells and antigen presenting cells to generate hybrids with characteristics of both the tumor and antigen presenting cell (Gong, J. et al. 1997, Nat. Med. 3:558–561). Non-modified, irradiated tumor cells have been injected into cancer patients in combination with adjuvants with considerable clinical effect (Vermorken, J. B. et al. 1999, Lancet 353:345–350). Insertion of lipid-modified proteins in the cell membrane of cancer cells builds on these findings and provides a vaccination strategy with autologous tumor cells with tailor-made properties. For example, it is within the scope of the invention to irradiated autologous tumor cells, endowed with LT-scFv specific for antigen-presenting cells and cytokines that stimulate antigen presenting cell expansion and maturation, are able to induce a vigorous anti-tumor response. Lipid-modification and expression of proteinaceous molecules in *E. coli* and their insertion into cell membranes is a general approach to temporarily endow a cell with single or multiple novel properties.

EXAMPLES

Materials and Methods

ScFv fragments

Most scFv fragments used in this study, selected from a semi-synthetic antibody phage display library, have been described previously (de Kruif, J. et al. 1995, J. Mol. Biol. 246: 97–105; de Kruif et al., 1995, Proc. Natl. Acad. Sci. USA. 92:3938–3942). The anti-CD32 scFv was selected by panning the library on recombinant CD32 protein coated in immunotubes (de Kruif, J. et al. 1995, J. Mol. Biol. 248: 97–105).

The anti-sheep red blood cell scFv was selected by panning on sheep red blood cells. The anti-CD14 scFv was selected on blood monocytes using flow cytometry (de Kruif et al., 1995, Proc. Natl. Acad. Sci. USA. 92:3938–3942). Specificities were verified using COS-7 cells transiently transfected with human CD14 or CD32 cDNA. The anti-CD64 scFv fragment (clone H22) (Graziano, R. F. et al. 1995, J. Immunol. 155:4996–5002) was a gift from Joel Goldstein, Medarex, Inc. Annandale, USA.

Vector construction.

Expression vector pLP2 was constructed by inserting a small hydrophilic linker (Pack, P. et al. 1993, Bio/technology. 11:1271–1277) into vector pLPscH (de Kruif et al. 1996, FEES lett. 399:232–236), (FIG. 1*a*). The full-encoded sequence of the N-terminus of LT-scFv proteins expressed in vector pLP2 is (SEQ ID NO:1):

MKATKLVLGAVILGSTLLAGCSSNAK-IDQPKPSTPPGSSAMA . . .

The LPP signal peptide and N-terminal amino acids are depicted in Italics, whereas the hydrophilic linker is shown in bold. The firs 3 amino acids of the LT-scFv are underlined, All protein coding sequences and the processing of the immature protein have been described in detail elsewhere (Laukkanen, M. L. et al. 1993, Protein Eng. 6:449–454; Laukkanen, M. L. et al. 1994, Biochemistry. 33:11664–11670; de Kruif, J. et al., 1996, FESS lett. 399:232–236; Pack, P. et al. 1993, Bio/technology. 11:1271–1277; Grayeb, J. et al. 1984, J. Biol. Chem. 259:463–467; and references therein)

One method to produce and purify lipid-modified molecules (standard protocol I). Production and purification of lipid-modified proteins are performed as described in detail (de Kruif et al., FEBS letters 399:232–236, 1996) and references therein. DNA encoding proteins of interest are cloned in vector pLP, resulting in the addition of an lpp lipidation signal, a myc tag for detection purposes and a polyhistidine tag for purification (FIG. 2). The resulting constructs are transformed in *E coli* SF110 F' strain and used as an inoculate in 250 ml 2TY medium. Cells are grown shaking at 25° C. until an $OD_{600mm}$ of 0.5 is reached. At this stage, IPTG is added to an end concentration of 1 mM. Incubation is continued overnight.

The next day, bacteria are harvested by centrifugation for 10 min. at 8000×g. Cell pellets are solubilized in 12 ml buffer A (20 mM hepes pH 7.4, 1M NaCl, 10% glycerol) containing 0.1 mg/ml lysozyme and allowed to sit at room temperature for 15 min. Preparations are then sonicated for 45 sec., on ice, in a sonicator. Thereafter, the protein preparations are centrifuged for 1 hr. at 100.000×g in an ultracentrifuge. The supernatant is discarded; the pellet is solubilized overnight in buffer A containing 1% Triton X-100. The preparations are centrifuged at 100.000×g for 1 hr. The pellet is discarded; the supernatant is diluted 5 times in buffer A containing 5 mM imidazole. The samples are run over a column packed with 1 ml nickel-agarose. The resin is washed using 10 ml LP buffer (20 mM hepes pH 7.4, 0.5 M NaCl, 1% B-D-octyl-glucanoside, 10% glycerol) containing 5 mM imidazole, followed by 2 ml LP buffer containing 50 mM imidazole. Proteins are eluted from the column using 2 ml LP buffer containing 200 mM imidazole. Samples are stored at −20° C. until further use.

One method of incorporation of lipid-modified molecules in cell membranes (standard protocol II). The cells of interest are washed once in ice cold 1% BSA in PBS followed by resuspension in he same buffer. Cells are counted and diluted to a concentration of $10^5$–$10^6$ cells/ml in Eppendorf vials. Twenty ml of the purified lipid-modified proteins are added per ml of cell suspension. The lipid-modified proteins are added by inserting a pipet tip halfway into the cell suspension and rapid ejection of the contents; tubes are closed immediately and the contents mixed by inverting the tube 10 times. The cells are incubated on ice for 30 min., washed once and resuspended in the appropriate buffer (eg. 1% BSA in PBS, or in cell culture medium)

The following examples describe the application, advantages and utility of the invention. To illustrate the method, we have used single chain Fv (scFv) antibody fragments as molecules that are capable of interacting with other soluble or membrane-bound molecules. In that respect, scFv antibody fragments serve as a model for a broad variety of molecules including receptors, co-receptors, membrane-bound ligands, signaling molecules, adhesion molecules and homing molecules. These examples are meant to illustrate, but not to limit, the spirit and scope of the invention.

Another method for production and purification of LT-scFv.

The production and purification of LT-scFv antibody fragments was performed as described (de Kruif, J. et al. 1996, PEPS lett. 399:232–236) Briefly, DNA encoding a scFv was cloned in vector pLP2, resulting in the addition of a lipidation signal, a linker, a myc tag for detection purposes and a polyhistidine tag for purification. The resulting constructs were expressed in the *E. coli* strain SF110 F'. Bacteria were harvested and LT-scFv purified from the membranes using detergent extraction and nickel-affinity chromatography. The modified scFv fragments were eluted in LP buffer (20 mM hepes pH 7.4, 0.5 M NaCl, 1% B-D-octyl-glucoside, 10% glycerol and 200 mM imidazole) and stored at −20° C. To monitor antibody yield and purity, preparations were routinely analyzed by SDS-PAGE and coomassie brilliant blue staining of gels (FIG. 1b).

Another method for the isolation of cells and incorporation of LT-scFv's into cell membranes.

All tissues were obtained wish informed consent Blood mononuclear cells from healthy donors and patients were isolated from heparinized blood by Ficoll (Pharmacia, Uppsala, Sweden) density centrifugation. Chronic lymphocytic lymphoma blood samples (CLL; $CD5^-$, $CD19^+$, $sIgM^+$) contained>95% tumor cells. A cell suspension of kidney tumor cells was prepared from a resection preparation from a patient with a Grawitz tumor as described (Grouard, G. et al. 1995, J. Immunol. 155:3345–3352)

For incorporation of LT-scFv, the cells were washed once in ice cold 1% BSA/PBS, counted and diluted in Eppendorf tubes to a concentratior of $10^5$–$10^6$ cells/ml in 1 ml 1% BSA in PBS.

Twenty $\mu$l of the purified LT-scFv corresponding to approximately 2 $\mu$g of protein was added per ml of cell suspension. The lipid-modified proteins were added by inserting a pipette tip halfway into the cell suspension and rapid ejection of the contents; tubes were closed immediately and the contents mixed by inverting the tube 6 times. The cells were incubated on ice for 30 min., washed once and resuspended in 1% BSA/PBS or cell culture medium. Detection and quantification of LT-scFv's in cell membranes.

Membrane-attached LT-scFv molecules were detected using monoclonal antibody 9E10 (ECACC, Salisbury, UK), specific for the myc-tag fused to the LT-scFv. A polyclonal goat anti-mouse antibody conjugated to the fluorochrome phycoerythrin (DAKO, Denmark) was used to detect cell-bound anti-myc antibody. Cells were analyzed by flow cytometry. A DAKO Qifi-kit (Dako, Denmark) was used for quantification of the number of scFv molecules per cell, following the protocol supplied by the manufacturer.

Proliferation and viability of LT-scFv-modified cells.

Jurkat cells were labeled with anti-dinitrophenol LT-scFv's, washed once in RPMI containing 10% fetal calf serum (RPMI-S), resuspended in the same medium and cultured at 37° C. Control cells were treated with LP buffer containing no LT-scFv fragments or were incubated in 1% BSA/PBS only. After various periods of time, samples were taken, stained with trypan blue to assess cell viability and counted using a haemocytometer.

Retention of cell-surface anchored scFv's at physiological conditions.

Figure 8:
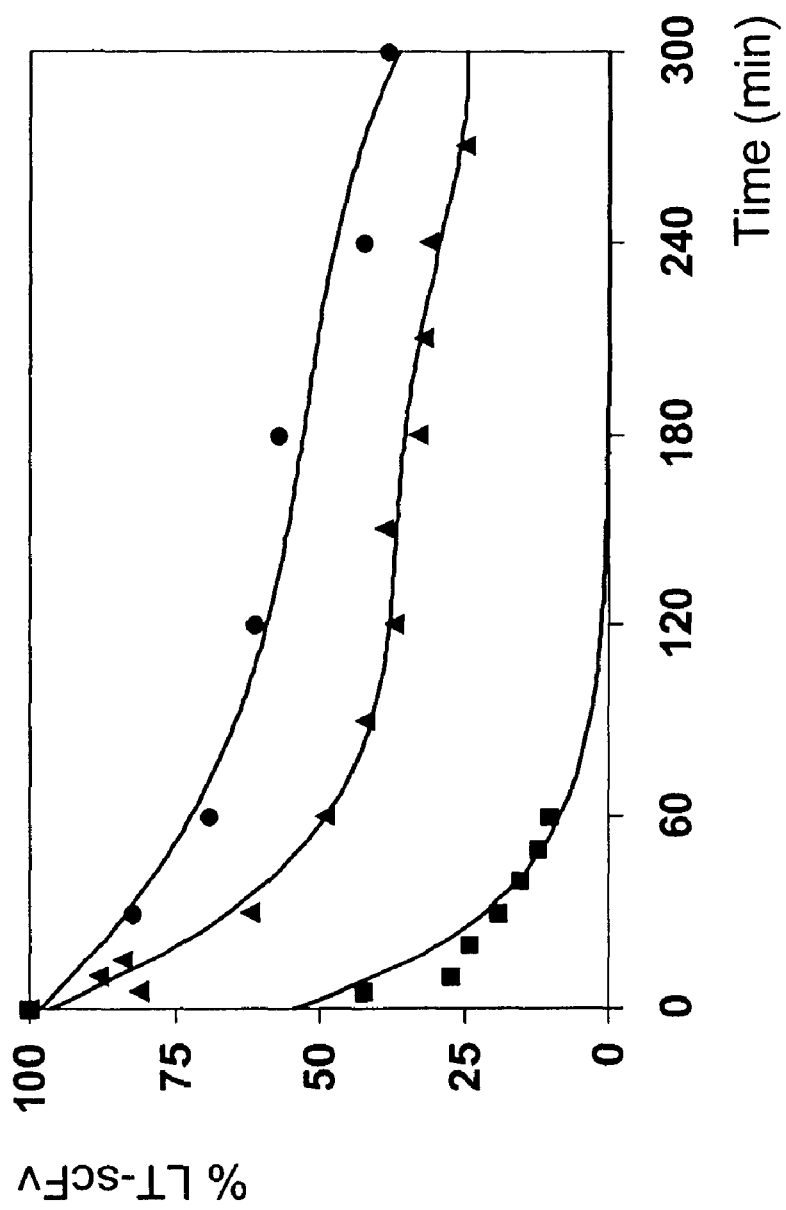

LT-scFv's specific for the hapten dinitrophenol were incorporated in the membranes of cell lines and freshly isolated cells. The cells were washed once in ice-cold RPMI-S and re-suspended in the same medium pre-warmed to 37° C. The cells were incubated at 37° C. in a $CO_2$ incubator. After various periods of time, samples were taken and the relative amount of LT-scFv present on the surface of the cells measured using flow cytometry. FACS data were gated on living cells, which did not reduce in number during the course of the experiment. In FIG. 8, the mean fluorescence intensity (MFI) at time-point 0 hr. was set at 100%; all other MFI's were calculated as a percentage of this value. Antigen binding of membrane-anchored LT-scFv's.

Jurkat T cells were incubated with an LT-scFv specific for purified human IgG and subsequently incubated with the human IgG conjugated to the fluorochrome fluoresceine isothiocyanate (FITC) at a concentration of 10 $\mu$g/ml in 1% BSA/PBS. Cells were washed twice and analyzed by flow cytometry. The controls consisted of the same procedure, except that the cells were incubated with an LT-scFv specific for the hapten dinitrophenol or with a murine FITC-labeled anti-tetanus toxoid monoclonal antibody. An LT-scFv antibody fragment specific for sheep red blood cells was incorporated into the membrane of the Daudi B cell line. Cells were washed and subsequently mixed with sheep red blood cells in a round-bottom test tube at room temperature. Cells were centrifuged for 1 min. at 100×g at room temperature and the tubes were incubated on ice for 1 hour. Aliquots were spotted on glass slides and visualized using a light microscope. The control consisted of the same procedure, except that the Daudi cells were incubated with an LT-scFv specific for dinitrophenol.

Phagocytosis of cells displaying a membrane anchored LT-scFv fragment.

Jurkat cells were labeled with the lipophilic dye PKH-26 (Sigma, St. Louis, USA) according to the protocol supplied by the manufacturer. Subsequently, LT-scFv's specific for CD14, CD32 or CD64, or a control LT-scFv specific for dinitrophenol were anchored to the cell membranes. Blood mononuclear cells were prepared and washed twice in RPMI-S. Approximately $10^5$ modified Jurkat cells were added to $10^6$ mononuclear cells in a total volume of 200 μl RPMI-S. This results in a Jurkat/monocyte ratio of ~1/1. The cells were incubated at 37° C. for 90 minutes, stained with a FITC-conjugated anti-CD14 antibody (Becton Dickinson, San Jose, USA) and resuspended in 1% paraformaldehyde in PBS. Cell-cell interaction and phagocytosis were monitored by flow cytometry and confocal laser scanning microscopy.

Example 1

Lipid-modified scFv are inserted into the plasma membrane in high numbers and specifically bind soluble antigen. The DNA encoding a scFv antibody fragment specific for an IgG paraprotein was cloned in vector pLP, expressed as a lipid-modified protein, purified and incorporated in the membrane of the Jurkat T cell line according to the standard protocols I and II. Membrane-attached scFv molecules were detected using a monoclonal antibody specific for the myc-tag fused to the carboxy-terminus of the lipid-modified scFv. A polyclonal goat anti-mouse antibody conjugated to the fluorochrome phycoerythrin was used to detect cell-bound anti-myc antibody. Cells were analysed on a FACScan flowcytometer. The control consisted of the same procedure, except that in the first step, the cells were incubated with LP buffer containing 200 mm imidazole (column elution buffer) instead of lipid-modified scFv. The results, shown in FIG. 3a, demonstrate the specific incorporation of the scFv in the cell membrane of Jurkat cells. Coupling of lipid modified scFv fragments, following this method, has been achieved in multiple cell lines, both non-adherent and adherent, and into freshly isolated peripheral blood leucocytes.

To estimate the number of scFv molecules attached in cell membranes, lipid modified scFv's specific for IgG paraprotein were incorporated in Jurkat and Daudi cells according to the standard protocols I and II. A DAKO Qifi-kit (Dako, Denmark) was used for quantification of the number of scFv molecules per cell, following the protocol supplied by the manufacturer. The number of scFv's was calculated to be 40.000–50.000 molecules per cell.

Jurkat cells were incubated with the lipid-modified scFv specific for the IgG paraprotein according to the standard protocols I and II and incubated with the IgG paraprotein conjugated to the fluorochrome fluoresceine isothiocyanate (FITC). Cells were washed and analysed on a flowcytometer. The control consisted of the same procedure, except that the cells were incubated with a lipid-modified scFv specific for the hapten dinitrophenol. This scFv does not bind to IgG paraprotein. The results, shown in FIG. 3b, demonstrate that Jurkat cells that have incorporated the lipid-modified scFv specifically bind soluble IgG paraprotein. These results demonstrate the principle that cells with membrane-attached scFv can bind soluble molecules present in the micro-environment of the cell.

Example 2

Cells with lipid-modified scFv inserted into the plasma membrane specifically bind membrane-bound antigens present on other cells.

The DNA encoding a scFv antibody fragment specific for sheep red blood cells was cloned in vector pLP, expressed as a lipid-modified protein, purified and incorporated in the membrane of the Daudi B cell line according to the standard protocols I and II. Cells were washed and subsequently incubated with sheep red blood cells in a round-bottom test tube at room temperature. Cells were centrifuged for 1 min. at 100xg at room temperature. The control consisted of the same procedure, except that the Daudi cells were incubated with a lipid-modified scFv specific for the human CD8 molecule that is not expressed by sheep red blood cells. The results, shown in FIG. 4, demonstrate that Daudi cells that have incorporated the scFv specific for sheep red blood cells bind to sheep red blood cells as visualised by the formation of rosettes (right panel) whereas Daudi cells that have incorporated the control scFv do not bind to sheep red blood cells as visualised by the absence of rosettes (left panel).

Example 3

Lipid-modified scFv's inserted in the plasma membranes of cells remain attached at physiological conditions. A lipid-modified scFv antibody fragment specific for sheep red blood cells was incorporated in the membranes of Daudi and Jurkat cells according to the standard protocol. The cells were washed once in ice cold RPMI containing 10% foetal calf serum, and resuspended in the same medium pre-warmed to 37° C. The cells were incubated at 37° C. in a $CO_2$ incubator. After various periods of time, samples were taken, washed once in ice-cold 1% BSA-PSS and the relative amount of scFv present at the surface of the cells measured using the Myc-tag specific monoclonal 9E10 and a flowcytometer. The results, shown in FIG. 5, indicate that approximately 50% of the molecules initially present after incorporating the lipid-modified scFv's into the cell membranes, can still be detected on these cells after 3 hours at 'physiological' temperatures. The stability is necessary to achieve therapeutic effect after re-introduction of cells manipulated to contain lipid-modified proteinaceous molecules into an organism.

Example 4

A number of proteins perform a function in signal transduction when present near or at membranes. A number of these proteins will, with the methods of the invention, be capable of altering the properties of a cell. Such molecules are, upon insertion into the membrane of said cells, capable of signal transduction via association with other membrane molecules or via inclusion in lipid rafts (Simons et al., Nature 387:569–572, 1997). In addition, lipid-modified proteinaceous molecules are genetically-engineered to introduce a domain that faciitates interaction with other membrane molecules that have signal transduction capabilities. Following this strategy, the cell harbouring the lipid-modified proteinaceous molecule is activated or induced to perform other cellular functions such as secretion of soluble molecules or cytotoxic activity.

Example 5

A lipid-modified scFv specific for micro-organisms such as bacteria and fungi is inserted in the plasma membrane of cells of the immune system that are capable of phagocytosis and elimination of micro-organisms. Such phagocytic cells can be pre-treated by cytokines to activate them and to enhance their phagocytic capacity. The scFv inserted in the plasma membrane of such cells serves as a recognition unit to further enhance the specificity and effectivety of the phagocytotic process, Example 6

A lipid-modified scFv recognising a structure on tumour cells is inserted into the plasma membrane of antigen-presenting cells such as dendritic cells and macrophages. Such cells are re-infused into cancer patients with the aim to direct the antigen-presenting cells to sites of tumour development. Upon recognition of tumour cells, the antigen presenting cells take up tumour cells and present processed tumour antigens to cells of the immune system. The application is carried out with the aim of inducing or enhancing anti-tumour immunoreactivity.

Example 7

A lipid-modified scFv recognising arterial plaques in patients with arteriosclerosis is inserted into the membrane of cells capable of breaking down plaques such as phagocytic cells. Such cells are re-infused into patients as a non-invasive therapy for arteriosclerosis.

Example 8

A scFv recognising the endothelial cells involved in the formation of novel blood vessels in developing tumours, a process known as angiogenesis, is inserted into the plasma membrane of effector cells of the immune system such as natural killer cells or granulocytes. Such cells are
re-infused into patients with the aim to direct the effector cells to the endothelial cells in the tumour and to destroy the tumour vasculature.

Example 9

The use of gene transfer to tumour cells in order to stimulate an anti-tumour immune response depends on the assumption that it is possible to break tolerance to tumour antigens (Houghton et al, J. Exp. Med. 180.1–4, 1994). By gene transfer and other studies, it has been demonstrated that expression of heat shock proteins (hsp) on the plasma membrane of tumour cells may be a key event to stimulate the immune system to eradicate the tumour cells (Melcher et al., Nature Medicine 5.581–587, 1998).

We isolated tumour cells from a colorectal tumour of a patient, and attached lipid-modified hsp proteins to the tumour cell plasma membrane. Upon re-infusions of the tumour cells, the immune system recognises and eradicates the tumour cells. The approach in this example can be combined with the approach outlined in example 6 to direct the tumour cells upon re-infusion in the patient effectively to antigen presenting cells. in this case, 2 different types of molecules are attached to the plasma membrane of a cell.

Example 10

To modify the target cell specificity of a lentiviral (HIV) based vector (Kafri et al, Nat Genet. 17, 314–317, 1997 and references therein) in the absence of the lentiviral envelop glycoprotein (env, for HIV called gp120) two functionalities need to be added to the vector. The first function that must be added is target cell specificity. This can be added in the form of a lipid-modified scFv specific for the desired target cell such as the lipid-modified scFv specific for the human CD8 molecule mentioned above. Instead of binding specifically to cells carrying the CD4 molecule on their membranes the virus now binds specifically to cells carrying the CD8 molecule on their surface, the so-called CD8 cells. The second function that needs to be added is a membrane fusion capacity. This function can be added to the virus membrane using a lipid-modified fusogenic peptide, Many fusogenic peptides are known in the art. One or more of these fusogenic peptides can be lipid-modified and transferred to the membrane of the virus particle.

Example 11

Cytotoxic T lymphocytes (CTLs) are responsible for the killing of tumour cells. In vivo priming of CTLs often requires the participation of T-helper lymphocytes (Keene et al., J. Exp. Med. 155, 168–782, 1982). T-helper cells express the CD40-ligand, a molecule that interacts with the CD40 molecule expressed on B cells and antigen-presenting cells such as dendritic cells and macrophages. After CD40—CD40-ligand interaction, the antigen presenting and co-stimulatory capacity of antigen-presenting cells greatly increases, resulting in the activation of CTLs (Bennett, et al., Nature 393, 478–480, 1998; Schoenberger et al., Nature 393, 480–483, 1998). With the subject method, lipid modified CD40-ligand or lipid-modified anti-CD40 scFv are inserted in the membrane of tumour cells in vitro and the modified tumour cells are re-infused in the patient. Thus, the tumour cell itself may provide the signal to activate antigen-presenting cells, by-passing the need for T helper cell activation, resulting in presentation of tumour cell antigens and anti-tumour immunity. Additional lipid-modified proteinaceous molecules may be inserted in the membrane of the tumour cells to further enhance the immunogenicity or the homing of the tumour cells.

Example 12

We have previously used vector pLPscH to produce lipid-tagged scFv (LT-scFv) fragments (de Kruif, J. et al. 1996, FEBS lett. 399:232–236).

In subsequent experiments, we noted that some LT-scFv, when inserted into the membranes of immunoliposomes, lost capacity to bind to their target antigen. The binding capacity was restored by using vector pLP2, inserting a flexible linker between the lipid tail and the scFv fragment, presumably by increasing the distance between the scFv binding site and the phospholipid membrane. Addition of the linker did not affect protein yields that ranged from 1.0 to 1.5 mg/liter of bacterial culture in shaker flasks. ScFv fragments not tagged by a lipid moiety, visible on SDS-PAGE gels as a protein band slightly smaller in size[1] could not be detected in the purified lipoprotein preparations (FIG. 1*b*).

FIG. 6*a* demonstrates the incorporation of LT-scFv antibody fragments specific for the hapten dinitrophenol into the cell membrane of Jurkat cells. Insertion of LT-scFv antibody fragments has been achieved in adherent and non-adherent cell lines of various lineages and in some gram-negative prokaryotes such as *E. coli* (FIG. 6*d*). Sheep red blood cells and gram-positive bacteria did not bind the LT-scFv as detected by FACS using anti-c-myc antibody. LT-scFv fragments could also be anchored to the membranes of freshly isolated cells including blood monocytes and tumor cells from a patient with a solid Grawitz kidney tumor and leukemic tumor cells from a patient with CLL (FIGS. 6b,c). Anchoring LT-scFv's to kidney tumor cells is somewhat less efficient, which can probably be attributed to the presence of cellular debris in these tissue preparations. The number of scFv's incorporated in the membranes of Jurkat and Daudi cells under standard conditions was calculated to be approximately $5 \times 10^4$ molecules per cell. Lower numbers of LT-scFv's could be attached to the cells by diluting the linoprotein samples in LP buffer; higher numbers of antibody fragments could )De aztached by repeatedly adding 20 µl of LT-scFv followed by washing of the cells (not shown). In all cases, virtually all cells in the reaction mixture were labeled with the LT-scFv's (FIG. 6). The insertion of LT-scFv's did not affect cell proliferation (FIG. 7), nor cell viability, which remained at ~96% up until 120 hr after addition of the TT-scFv's, To monitor the stability of membrane-anchored LT-scFv's under physiological conditions, Jurkat cells, freshly-isolated tumor cells from a patient with CLL, and peripheral blood-derived monocytes were incubated with LT-scFv's, resuspended in RPMI-S medium and incubated at 37° C. for various periods of time before flow cytometric analysis. The number of scFv molecules detectable in the cell membrane as a function of time followed a bi-phasic course representing a relatively rapid initial decline sloping off into a more gradual decrease. A difference in the kinetics was noted when comparing the cell types. in the Jurkat cell line and CLL tumor cells, 50 of the scFv molecules was lost after almost five hours and one hour respectively, whereas in the monocytes 50% of the LT-scFv's was lost within minutes. In the Jurkat cells, scFv could still be detected after 24 hours at 37° C.

Figures 9A, 9B:
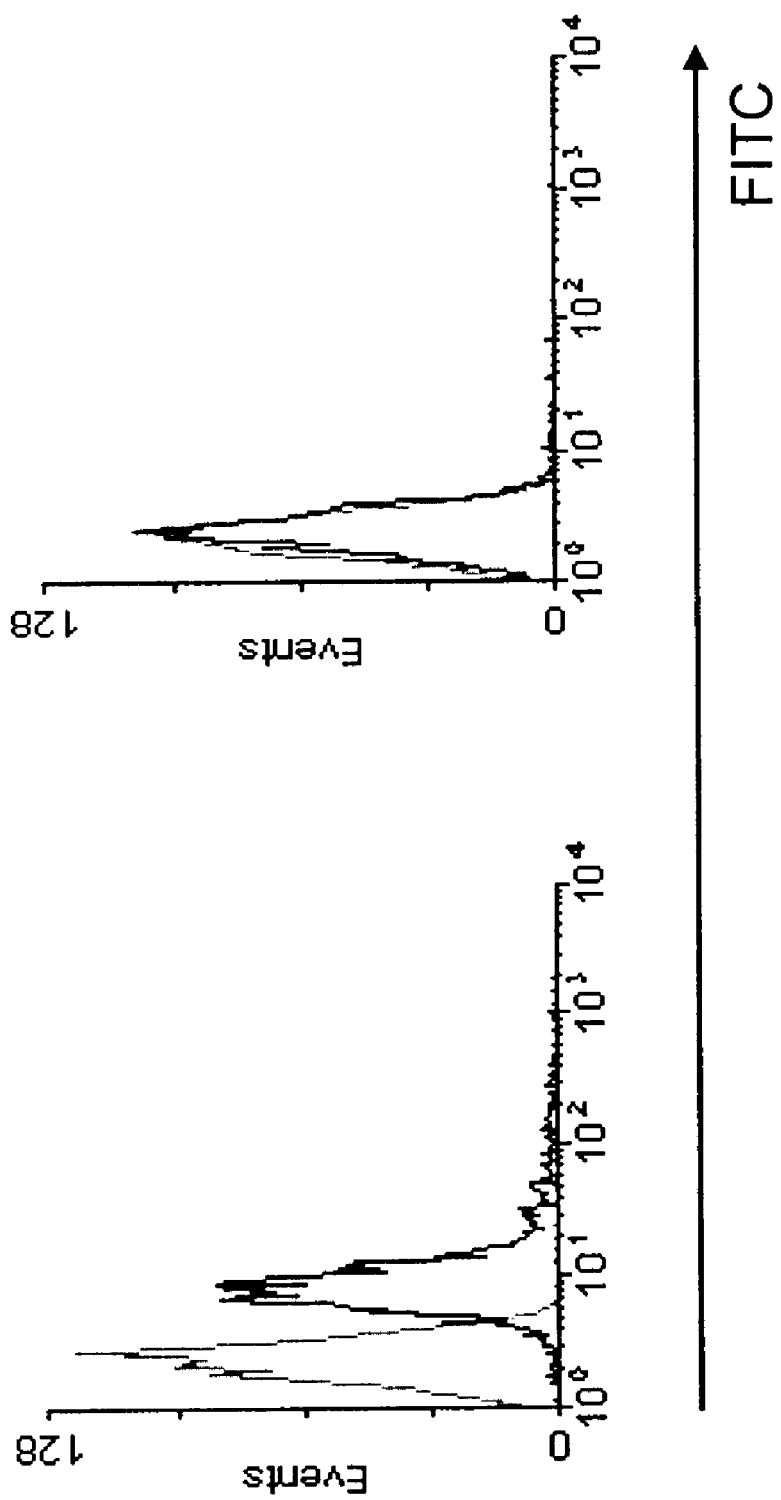
Figure 9C:
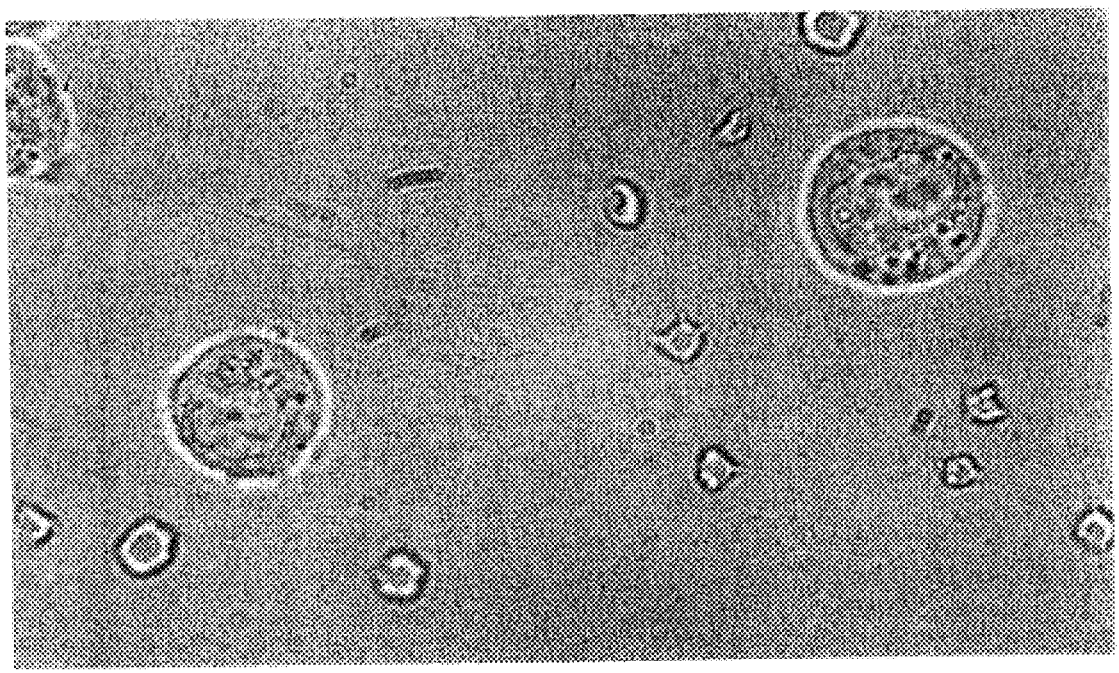
Figure 9D:
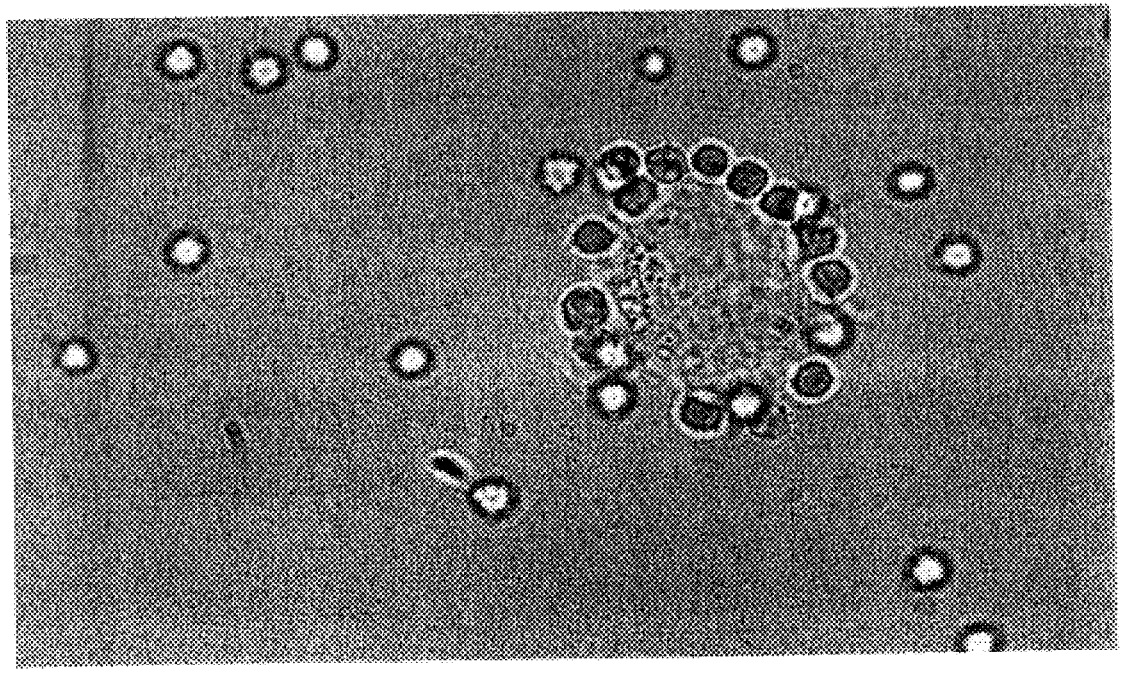

To demonstrate that LT-scFv antibody fragments coupled to cell membranes retain the capacity to hind their target antigen, Jurkat cells were incubated with an LT-scFv fragment specific for human IgG and subsequently exposed to tire FITC-labeled human IgG. Flow cytometric analysis (FIGS. 9a,b) shows that cells with membrane-atlached LT-scFv specifically bind soluble IgG-FITC, We next assessed the capability of LT-scFv to mediate cell—cell interaction. Daudi cells with membrane-incorporated LT-scFv's specific for sheep red blood cells were incubated with sheep red blood cells. Daudi cell-red blood cell interaction was visualized by the formation of rosettes. No rosette formation was observed when a control LT-scFv specific for dinitrophenol was incorporated into the Daudi cell membrane (FIGS. 9c,d).

Figure 10E:
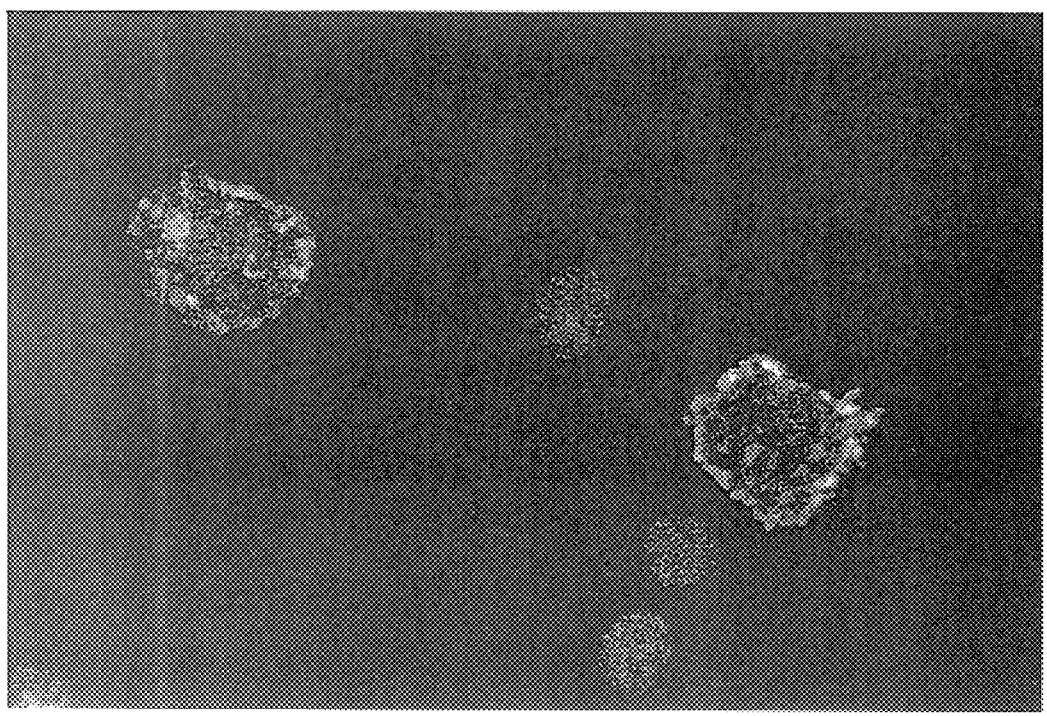

To demonstrate that membrane-anchored LT-scFv fragments can be used to provide a cell with novel functional properties, LT-scFv fragments specific for CD14, CD32 or CD64 were inserted into the membrane of red-labeled Jurkat cells. The Jurkat cells were subsequently incubated with a suspension of blood mononuclear cells containing monocytes that express CD14, CD32 and CD64, and the cells were allowed to interact at 37° C. Thereafter the monocytes were visualized using a FITC-labeled anti-CD14 monoclonal antibody. Insertion of a control LT-scFv in the Jurkat cells did not result in the formation of double-positive cells (FIG. 10a). Insertion of the anti-CD14 (FIG. 10b), anti-CD32 (FIG. 10c) or anti-CD64 (FIG. 10d) LT-scFv's into the membrane of Jurkat cells mediated interaction with monocytes, as visualized by the presence of double-positive cells. Confocal laser scan microscopy confirmed that the red fluorescent dye resides in the cellular interior of the green-labeled monocytes, consistent with phagocytosis of the Jurkat cells (FIG. 10e, shown for the anti-CD14 LT-scFv experiment; identical pictures were obtained when anti-CD32 or anti-CD64 LT-scFv's were used). Similar results were obtained in experiments with CEM and RAJI T and B lymphocyte target cell lines respectively and with monocyte-derived macrophages as phagocytes (not shown). To establish whether molecules other than scFv antibody fragments could be lipid-modified and inserted into cell membranes, the gene encoding human interleukin-2 (IL-2) was cloned into vector pLP2 and lipid-tagged IL-2 (LT-IL-2) was purified from E. coli cells. Purified LT-IL-2 was incubated with RPMI 8226 cells and insertion into the membrane was monitored by flow cytometry using a phycoerythrin-labeled anti-human IL-2 antibody. The results showed that LT-IL-2 could be incorporated into the membrane with an efficiency comparable to that of the LT-scFv fragments.

Upon further study of the specification, drawings and appended claims, further objects and advantages of this invention will become apparent to those skilled in the art.

LEGENDS TO THE FIGURES

FIGS. 1A–1C
a) Schematic representation of vector pLP2 used for expression of LT-scFv fragments. P, LacZ promoter/operator region; L, E. coli lipoprotein sequences; H, hinge linker sequence; S, scFv sequence; M, myc tag sequence; 6, polyhistidine stretch. The black arrow points at the acylation site.
b) Coomassie brilliant blue stained SDS-PAGE gel of a purified LT-scFv preparation.
c) Schematic outline of the procedure. LT-scFv proteins are expressed in E. coil bacteria, purified and mixed with cells, resulting in incorporation of functional antibody fragments into the cell membranes.

FIGS. 2A–2B
Panel A: schematic representation of the construct in vector pLP. P/0, lacZ promotor-operator region; lpp, E. coli lipoprotein sequences; scFv, variable domain antibody fragment; M, myc-tag; H, hexahistidyl tag. Panel B: schematic representation of a lipid-modified scFv inserted into the plasma membrane.

Figures 3A, 3B:
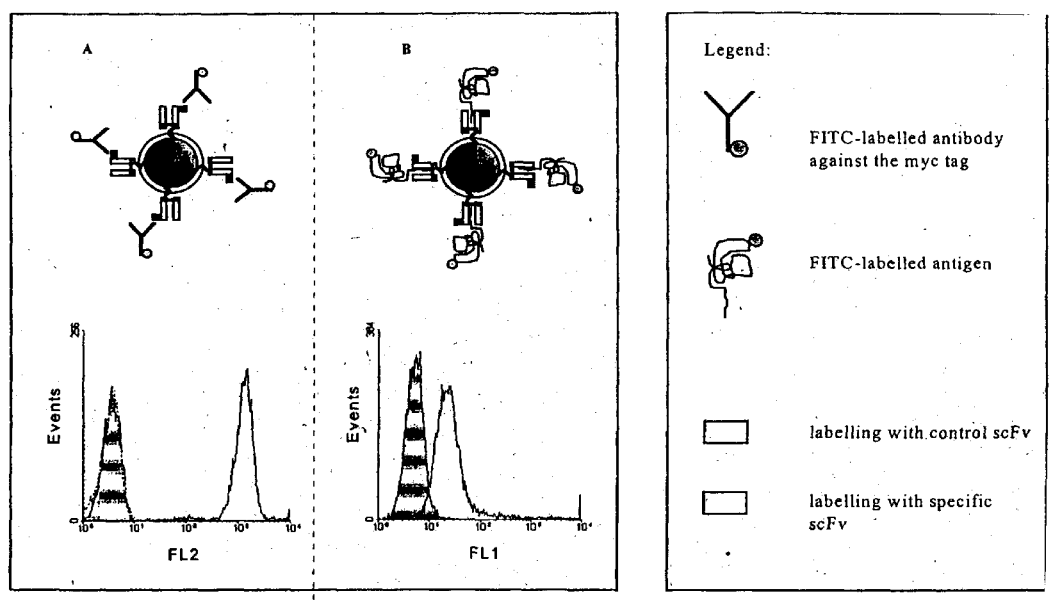

FIGS. 3A–3B
Incorporation of lipid-modified scFv fragments into cell membranes. A) scFv fragments were attached to membranes of Jurkat T cells as described in the general protocols I and II and detected using flow cytometry using a phyco-erythrin-labelled anti-myc tag monoclonal antibody. White peak/dashed line: untreated cells; grey peak: cells incubated in LP buffer alone; white peak/solid line: cells incubated in LP buffer containing a lipid-modified scFv fragment. B) An anti-IgG lipid-modified scFv, or a control lipid-modified scFv was incorporated into cell membranes as described. Cells were then incubated with FITC-labelled IgG. Bound IgG was detected using flowcytometry. The grey peak represents cells treated with a control anti-dinitrophenol lipid-modified scFv; the white peak represents cells treated with the anti-IgG lipid-modified scFv.

Figure 5:
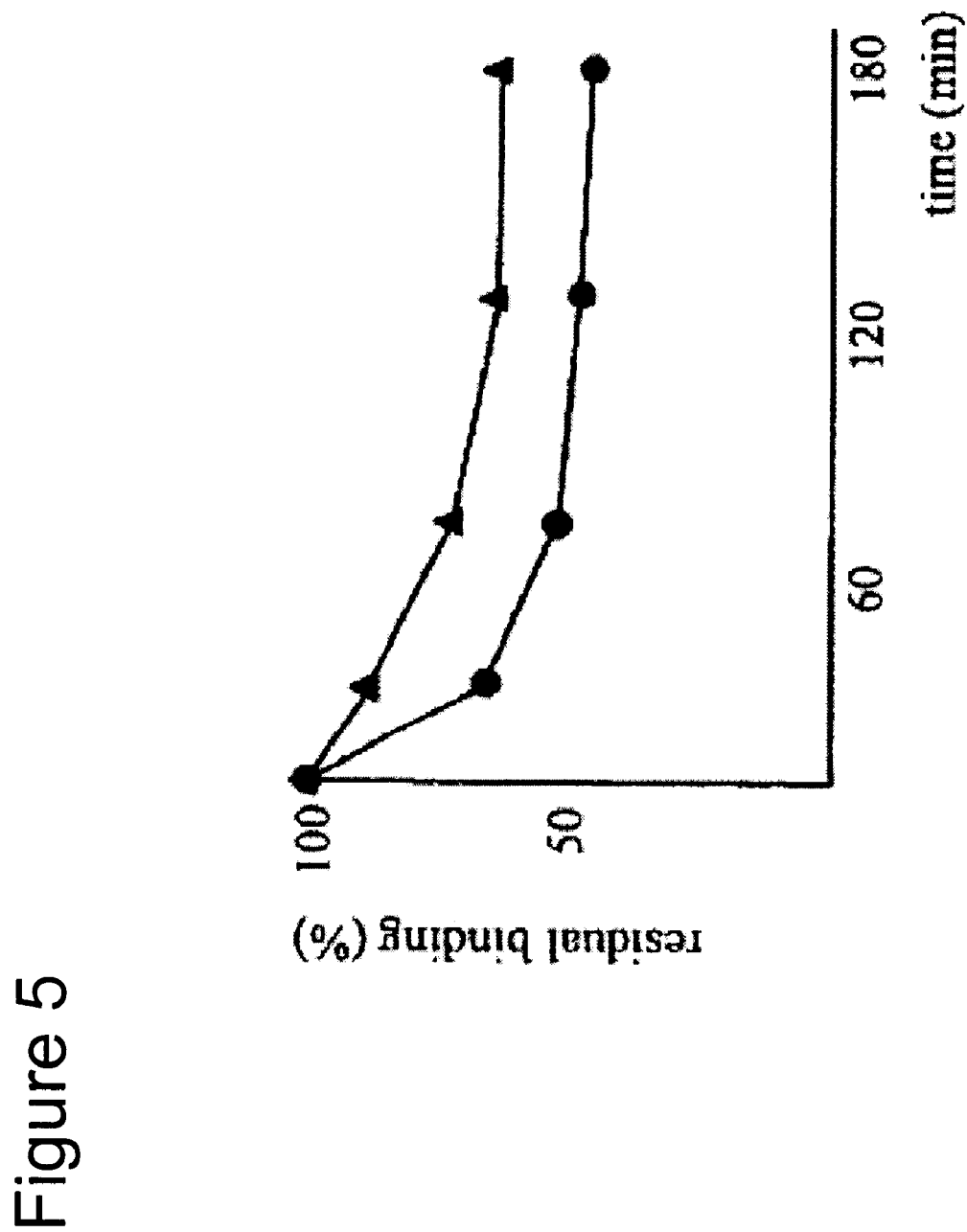

FIGS. 4A–4B
Cell-cell interaction mediated by a lipid-modified scFv inserted into the plasma cell membrane of one of the interacting partners. A lipid-modified scFv specific for red blood cells, or a control lipid-modified scFv specific for dinitrophenol, were incorporated into the membrane of Daudi B cells. The manipulated Daudi cells were subsequently mixed with sheep red blood cells and visualised under a light microscope. The right panel represents the interaction (formation of rosettes) of Daudi cells and sheep red blood cells mediated by the sheep red blood cell-specific lipid-modified scFv. The left panel represents the lack of interaction (no formation of rosettes) of Daudi cells and sheep red blood cells when the control dinitrophenol-specific, lipid-modified scFv is used.
FIG. 5

Figure 7:
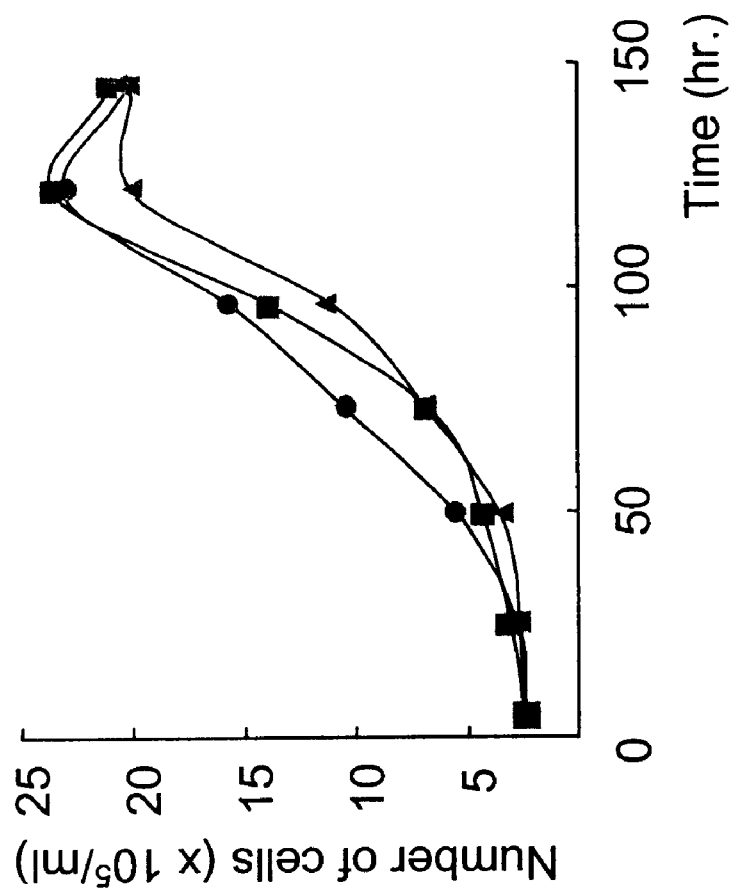

Retention of lipid-modified scFv fragments in eukaryotic cell membranes. Lipid-modified-scFv fragments were incorporated in the plasma membranes of Daudi (triangles) and Jurkat (circles) cells using the standard protocols I and II, and incubated at 37° C. for various periods of time before flowcytometric analysis. Membrane-bound lipid-modified scFv's were detected as described in the legend to FIG. 3.
FIGS. 6A–6B Incorporation of lipid-modified scFv fragments into cell membranes. Anti-dinitrophenol LT-scFv fragments were attached to membranes of Jurkat cells (a), freshly isolated kidney tumor cells (b) tumor cell derived from a patient with CLL (c) and *E. coli* bacteria (d), and detected using the anti-myc tag antibody and flow cytometry. Grey lines, cells incubated in LP buffer alone; black lines, cells incubated in LP buffer containing the LT-scFv fragment.
FIG. 7

Proliferation of Jurkat cells containing membrane-anchored anti-dinitrophenol LT-scFv fragments. LT-scFv fragments were incorporated into the plasma membranes of Jurkat cells. Cells were then put back into culture and counted daily. ▼: cells incubated in 1% BSA in PBS alone; •: LP buffer without LT-scFv's added; ■: LP buffer containing LT-scFv's. Viability remained at ~96 up to 120 hr. after addition of the LT-scFv's for all conditions used, as measured by trypan blue exclusion.
FIG. 8

Retention of lipid-modified scFv fragments in eukaryotic cell membranes. Lipid-modified scFv fragments were incorporated into the plasma membranes of Jurkat cells (•), tumor cells derived from a patient with CLL (▼) or PBL derived monocytes (■) and incubated at 37° C. for various periods of time before flow cytometric analysis. The amount of LT-scFv present at time point 0 hr. is set at 100%. All other values are calculated as a percentage of these values.
FIGS. 9A–9D Binding of membrane anchored LT-scFv to target antigens. An anti-human IgG LT-scFv, or a control LT-scFv was incorporated into Jurkat cell membranes. Cells were then incubated with FITC-labeled human IgG (a) or a control FITC labeled protein not recognized by this scFv fragment (b).

Attached proteins were detected using flow cytometry. Grey lines represent cells treated with a control anti-dinitrophenol LT-scFv; the black lines represent cells treated with the anti-human IgG LT-scFv.

An LT-scFv specific for sheep red blood cells (c), or a control LT-scFv specific for dinitrophenol (d), was attached to the membranes of Daudi cells. The cells were then mixed with sheep red blood cells and visualized under a light microscope,
FIGS. 10A–10E Phagocytosis of LT-scFv modified Jurkat cells by monocytes. Mononuclear cells were mixed with Jurkat cells modified to contain both a red fluorescent dye and an LT-scFv fragment. The cells were allowed to interact for 90 minutes at 37° C., stained with a green anti-CD14 FITC to identify the monocytes and analyzed using flow cytometry. (a), Jurkat cells displaying a control anti-dinitrophenol LT-scFv; (b), Jurkat cells displaying the anti-CD14 scFv; (c), Jurkat cells displaying the anti-CD64 scFv fragment; (d), Jurkat cells displaying the anti-CD32 scFv fragment. Numbers shown in the figures represent the percentage of total $CD14^+$ cells that stain double positive. Cells from sample (b) were fixed on a glass slide and visualized using a confocal laser scanning microscope (e). Individual red Jurkat cells and a green monocyte are visible in addition to a double positive monocyte that has phagocytosed a Jurkat cell.

References

1. Laukkanen, M. L., Teeri, T. T. and Keinanen, K. (1993). Lipid-tagged antibodies: bacterial expression and characterization of a lipoprotein-single-chain antibody fusion protein. Protein Eng. 6:449–454.
2. Laukkanen, M. L., Alfthan, K. and Keinanen, K. (1994). Functional immunoliposomes harboring a biosynzhetically lipid-tagged single-chain antibody. Biochemistry. 33:11664–11670.
3. de Kruif, J., Storm, G. van Bloois, L., and Logtenberg, T. (1996). Biosynthetically lipid-modified human scFv fragments from phage display libraries as targeting molecules for immuroliposomes. FEBS lett. 399.232–236.
4. de Kruif, J., Boel, E., and Logtenberg, T. (1995). Selection and application of human single chain Fv antibody fragments from a semi-synthetic phage antibody display library with designed CDR3 regions. J. Mol. Biol. 248: 97–105.
5. de Kruif, J., Terstappen, L., Boel, E. and Logtenberg T. (1995). Rapid selection of cell subpopulation-specific human monoclonal antibodies from a synthetic phage antibody library. Proc. Natl. Acad. Sci. USA. 92:3938–3942.
6. Graziano, R. F. et al. (1995). Construction and characterization of a humanized anti-gamma-Ig receptor type I FcγRI) monoclonal antibody. J. Immunol. 155:4996–5002.
7. Pack, P. et al. (1993). Improved bivalent miniantibodies, with identical avidity as whole antibodies, produced by high cell density fermentation of *Escherichia coli*. Bio/technology. 11:1271–1277.
8. Grayeb, J. and Inouye, M. (1984). Nine amino acid residues at the NH2-terminal of lipoprotein are sufficient for its modification, processing and localization in the outer membrane of Escherichia coli. J. Biol. Chem. 259:463–467.
9. Grouard, G., de Boutteiller, O., Banchereau, J. and Liu, Y-J. (1995). Human follicular dendritic cells enhance cytokine-dependent growth and differentiation of CD40-activated B-cells. J. Immunol. 155:3345–3352.
10. Smiths, G. P. (1985). Filamentous fusion phage: novel expression vectors that display cloned antigens on the virion surface. Science. 228:1315–1317.
11. Francisco, J. A., Earhart, C. F. and Georgiou, G. (1992). Transport and anchoring of beta-lactamase to the external surface of *Escherichia coli*. Proc. Natl. Acad. Sci. USA. 89:2713–2717.
12. Boder E. T. and Wittrup, K. D. (1997). Yeast surface display for screening combinatorial polypeptide libraries. Nat. Biotechnol. 15:553–557.
13. Eshhar, Z. (1997). Tumor-specific T-bodies: towards clinical application. Cancer Immunol. Immunother. 45:131–13614. Kwiatkowska, K. and Sobota, A. (1999). Signaling pathways in phagocytosis. BicEssays. 21:422–431.
15. Devitt, A. et al. (1998). Human CD14 mediates recognition and phagocytosis of apoptotic cells. Nature 392:505–509.
16. Sallusto, F and Lanzavecchia, A. (1994). Efficient presentation of soluble antigen by cultured human dendritic cells is maintained by granulocyte/macrophage colony-stimulating factor plus interleukin 4 and down-regulated by tumor necrosis factor alpha. J. Exp. Med. 179: 1109–1114.
17. Gosselin, E. J., Wardwell, K., Gosselin, D. R., Alter, N. Fisher, J. L. and Guyre, P. M. (1992). Enhanced antigen presentation using human Fcγ receptor (monocyte/macrophage)-specific immunogens. J. Immunol. 149:3477–3481.
18. Liu, C. et al. (1999). FcγRI-targeted fusion proteins result in efficient presentation by human monocytes of antigenic and agonist cell epitopes. J. Clin. Invest. 98:2001–2007.
19. Ridge, J. P., Di Rosa, F., Matzinger P.(1998). A conditioned dendritic cell can be a temporal bridge between a CD4+ T-helper and a T-killer cell. Nature. 393:474–478.
20. Nawrocki, S. and Mackiewicz, A. (1999). Genetically modified tumour vaccines-where we are today. Cancer Treat. Rev. 25:29–46.
21. Schirrmacher, V., et al. (1999). Human tumor cell modification by virus infection. Gene Ther. 6:63–73.
22. Haas, C., Herold-Mende, C., Gerhards, R. and Schirrmacher, V. (1999). An effective strategy of human tumor vaccin modification by coupling bispecific costimulatory molecules. Cancer Gene Ther. 6:254–262.
23. Berd, D. et al. (1998). Autologous, hapten-modified vaccine as a treatment for human cancers. Semin. Oncol. 25: 646–653.
24. Gong, J., Chen, D., Kashiwaba, M. and Kufe, D. (1997). Induction of antitumor activity by immunization with fusions of dendritic and carcinoma cells. Nat. Med. 3:558–561.
25. Vermorken, J. B. et al. (1999). Active specific immunotherapy for stage II and stage III human colon cancer: a randomized trial. Lancet 353:345–350.

wherein said lipid-modified protein is enzymatically synthesized to contain bound lipid either in a cell or in a cell-free system from a fusion protein that has at least one first portion derived from said first heterologous protein and at least one second portion comprising a lipidation signal derived from a second protein, wherein said second protein is a lipoprotein, wherein the effective amount is sufficient to impart to the target cell and/or target cell membrane surface an additional characteristic resulting from the first heterologous portion, and the lipid bound to the lipid-modified protein attaches the lipid-modified protein directly to the target cell and/or target cellular membrane.

2. The process according to claim 1 wherein at least part of the assembly of the lipid-modified protein is performed in a cell.

3. The process according to claim 1 wherein said lipidation signal is derived from a bacterial lipoprotein (lpp).

4. The process according to claim 1 wherein at least part of said first portion is derived from a protein of the immune system.

5. The process according to claim 1 wherein at least part of said first portion is derived from a fragment antigen binding (FAB) antibody fragment.

6. The process according to claim 1 wherein at least part of said first portion comprises a receptor, co-receptor, ligand, homing molecule, adhesion molecule, heat shock protein, signaling protein or pump.

7. The process according to claim 1 wherein at least part of said first portion comprises a stretch of amino acids conferring to said lipid-modified protein the property to interact with a signal-transducing molecule present on the plasma membrane of said cell.

8. The process according to claim 1 wherein said lipid-modified protein has a purification tag.

What is claimed is:

1. A process for altering the properties of a target cell and/or a target cellular membrane through the direct introduction of a first heterologous protein to the target cell and/or target cellular membrane surface comprising contacting said target cell and/or target cellular membrane with an effective amount of a lipid-modified protein, 9. The process according to claim 1 wherein said lipid-modified protein has a detection tag.

10. The process according to claim 1 wherein the target cell or target cellular membrane is a eukaryotic cell or eukaryotic cellular membrane.

11. A target cell or a particle comprising a membrane derived from said target cell, comprising a lipid-modified protein, said cell or said particle obtained by the process according to claim 1.

12. The process according to claim 4 wherein at least part of said first portion is derived from a single chain variable antibody fragment.

13. A therapeutic composition comprising a cell or cellular membrane according to claim 11.

14. The process according to claim 12 wherein said single chain variable antibody fragment has a lipid-bound protein portion at the amino-terminus and a lipid-bound protein portion at the carboxy-terminus.

15. A process for altering the properties of a target cell and/or a target cellular membrane through the direct introduction of a first heterologous protein to the target cell and/or target cellular membrane surface comprising contacting said target cell and/or target cellular membrane with an effective amount of a lipid-modified protein, wherein said lipid-modified protein is enzymatically synthesized to contain bound lipid either in a cell or in a cell-free system from a fusion protein that has at least one first portion derived from said first heterologous protein and at least one second portion comprising a lipidation signal derived from a second protein, wherein the effective amount is sufficient to impart to the target cell and/or target cell membrane surface an additional characteristic resulting from the first heterologous portion, and the lipid bound to the lipid-modified protein attaches the lipid-modified protein directly to the target cell and/or target cellular membrane, and wherein at least part of said first portion is derived from a single chain variable antibody fragment.

16. The process according to claim 15 wherein said single chain variable antibody fragment has a lipid-bound protein portion at the amino-terminus and a lipid-bound protein portion at the carboxy-terminus.

17. The process according to claim 15 wherein the target cell or target cellular membrane is a eukaryotic cell or eukaryotic cellular membrane.

18. The process according to claim 15 wherein said lipidation signal is derived from a lipoprotein.

19. A process for altering the properties of a target cell and/or a target cellular membrane through the direct introduction of a first heterologous protein to the target cell and/or target cellular membrane surface comprising contacting said target cell and/or target cellular membrane with an effective amount of a lipid-modified protein, wherein said lipid-modified protein is enzymatically synthesized to contain bound lipid either in a cell or in a cell-free system from a fusion protein that has at least one first portion derived from said first heterologous protein and at least one second portion comprising a lipidation signal derived from a second protein, wherein the effective amount is sufficient to impart to the target cell and/or target cell membrane surface an additional characteristic resulting from the first heterologous portion, and the lipid bound to the lipid-modified protein attaches the lipid-modified protein directly to the target cell and/or target cellular membrane, and wherein said lipid-modified protein has a detection tag.

20. The process according to claim 19 wherein the target cell or target cellular membrane is a eukaryotic cell or eukaryotic cellular membrane.

21. The process according to claim 19 wherein said lipidation signal is derived from a lipoprotein.

* * * * *

SEQUENCE LISTING

<160> NUMBER OF SEQ ID NOS: 1

<210> SEQ ID NO 1
<211> LENGTH: 42
<212> TYPE: PRT
<213> ORGANISM: Artificial Sequence
<220> FEATURE:
<223> OTHER INFORMATION: Description of Artificial Sequence: Constructed peptide

<400> SEQUENCE: 1

Met Lys Ala Thr Lys Leu Val Leu Gly Ala Val Ile Leu Gly Ser Thr
1               5                   10                  15

Leu Leu Ala Gly Cys Ser Ser Asn Ala Lys Ile Asp Gln Pro Lys Pro
            20                  25                  30

Ser Thr Pro Pro Gly Ser Ser Ala Met Ala
        35                  40